United States Patent
Fridman et al.

(10) Patent No.: US 7,756,644 B2
(45) Date of Patent: Jul. 13, 2010

(54) SYSTEM AND METHOD FOR AUTOMATED SELECTION OF T-CELL EPITOPES

(75) Inventors: Arthur Fridman, Brooklyn, NY (US); Ansuman Bagchi, Plainsboro, NJ (US); Wendy Bailey, Fort Washington, PA (US)

(73) Assignee: Merck & Co., Inc., Rahway, NJ (US)

( * ) Notice: Subject to any disclaimer, the term of this patent is extended or adjusted under 35 U.S.C. 154(b) by 475 days.

(21) Appl. No.: 11/430,214

(22) Filed: May 8, 2006

(65) Prior Publication Data

US 2006/0257944 A1 Nov. 16, 2006

Related U.S. Application Data

(60) Provisional application No. 60/680,323, filed on May 12, 2005.

(51) Int. Cl.
*G01N 33/53* (2006.01)
*G06F 19/00* (2006.01)
*C12Q 1/70* (2006.01)

(52) U.S. Cl. .......................... 702/19; 703/11; 530/350; 435/7.1

(58) Field of Classification Search .................. 703/11; 702/19
See application file for complete search history.

(56) References Cited

U.S. PATENT DOCUMENTS 5,747,269 A   5/1998   Rammensee et al.
6,037,135 A   3/2000   Kubo et al.
6,602,510 B1  8/2003   Fikes et al.
2004/0072249 A1  4/2004  Hoffman et al.
2005/0074809 A1*  4/2005  Brusic .................. 435/7.1

OTHER PUBLICATIONS

Burden et al. Predictive Bayesian neural network models of MHC class II peptide binding. Journal of Molecular Graphics and Modelling vol. 23, Issue 6, Jun. 2005 (available online May 6, 2005), pp. 481-489.*

Gribskov, et al., "Profile analysis: Detection of distantly related proteing", PNAS, vol. 84, pp. 4355-4358, 1987.

(Continued)

*Primary Examiner*—Michael Borin
(74) *Attorney, Agent, or Firm*—Alysia A. Finnegan; Sheldon O. Heber

(57) ABSTRACT

Methodology for the automated selection and/or optimization of T-cell epitopes is disclosed. The invention provides a data processing system which utilizes sequence-based statistical pattern recognition to compute an epitope selection matrix based on the informational content of epitopes known to bind to a particular major histocompatibility class I allele. The resulting Bayes-corrected scoring matrix is used to predict the relative binding affinities of candidate T-cell epitopes derived from immunologically relevant antigens of self or foreign origin. One aspect of the invention describes an analytical method for identification of modifications in known or predicted T-cell epitopes that confer upon the epitopes the ability to elicit stronger cellular immune response due to more efficient processing and/or presentation to T-cells. The disclosed epitope identification algorithm is applicable to the design of vaccines for infectious diseases, cancer and autoimmune diseases as well as for developing methods for the in vitro evaluation of cellular immunity.

14 Claims, 6 Drawing Sheets

OTHER PUBLICATIONS

Figure 1A:
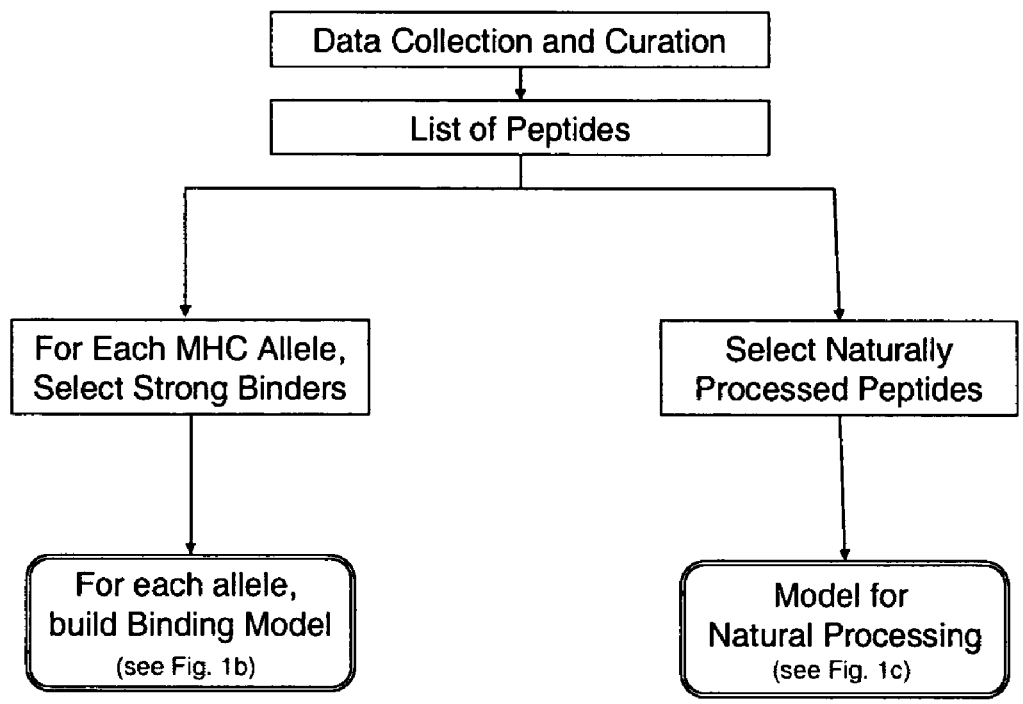

Correale, et al., "In Vitro Generation of Human Cytotoxic T Lymphocytes Specific for Peptides Derivied from Prostate-Specific Antigen", Journal of the National Cancer Institiute, vol. 89, No. 4, pp. 293-300, 1997.

Falk, et al., "Allele-specific motifs revealed by sequencing of self-peptides eluted from MHC molecules", Nature, vol. 35, pp. 290-296, 1991.

O. Rotzschke, et al., "Exact predicition of a Natural T cell epitope", Eurology Journal of Immunology, vol. 21, pp. 2891-2894, 1991.

A. Sette, et al., "The Relationship Between Class 1 Binding Affinity and Immunogenicity of Potential Cytotoxic T Cell Epitopes", Journal of Immunology, pp. 5586-5592, 1994.

K. Parker, et al., "Scheme for Ranking Potoential HLA-A2 Binding Peptides Based on Independent Binding of Individual Peptide Side-Chains", Journal of Immunology, pp. 163-175, 1994.

H. Snyder, et al., "Trimming of anitgenic peptides in an early secretory compartment", Journal of Exp. Medical, pp. 2389-2394, 1994.

Lipford, et al., "Peptide engineering allows cytotoxic T-cell vaccination against human papillomavirus tumor antigen E6", Immunology, pp. 298-303, 1995.

M. Parkhurst, et al., "Induction of Melanoma-Reactive CTL with Peptides from the Melanoma Antigen gp100 Modified at HLA-A*0201-Binding Residues", Journal of Immunology, pp. 2539-2548, 1996.

H. Rammensee, et al., "MHC ligands and peptide motifs-History and overview", Landes Bioscience, pp. 1-16, 1997.

F. Garcia F, et al., "Lack of carboxyl-terminal tyrosine distinguishes the B*2706-bound peptide repertoire from those of B*2704 and other HLA-B27 subtypes associated to ankylosing spondylitis", Tissue Antigens, pp. 215-221, 1997.

S.F. Altschul, et al., "Gapped BLAST and PSI-BLAST: a new generation of protein database search programs", Nucleic Acids Research, pp. 3389-3402, 1997.

D. Pardoll, et al., "The role of CD4*T cell responses in antitumor immunity", Curr Opinion Immumology, pp. 588-594, 1998.

H. Rammensee, et al., "SYFPEITHI: database for MHC ligands and peptide motiffs", Immunogentics, pp. 89-97, 1999.

P. Scognamiglio, et al., "Presence of Effector DC8+ T Cells in Hepatitis C Virus-Exposed Healthy Seronegative Donors", Journal of Immunology, pp. 6681-6689, 1999.

A. Van Elsas, et al., combination Immunotherapy of B16 Melonoma Using Anti-Cytotoxic T Lymphocyte-associated Antigen 4 (CTLA-4) and Granulocyte/Macrophage Coloby-Stimulating Factor (GM-CSF)-producing Vaccines Induces Rejection of Subcutaneous and Metastic Tumors Accompanied by Autoimmune Depigmentation, Journal of Exp Medicine, pp. 355-366, 1999.

W. Herr, et al., "Identification of naturally processed and HLA-presented Epstein-Barr virus peptides recognized by CD4+ or CD8+ T lymphocytes from human blood", PNAS, pp. 12033-12038, 1999.

Scardino, et al., "Identification of HER-2/neu immunogenic epitopes presented by renal cell carcinoma and other human epithelial tumors", Eurology Journal of Immunology, pp. 3261-3270, 2001.

B. Ludewig, et al., "Immunotherapy with Dendritic Cell Directed against Tumor Antigens Shared with Normal Host Cells Results in Severe Autoimmune Disease", Journal of Exp. Medicine, pp. 795-804, 2000.

E. Keogh, "Identification of New Epitopes from Four Different tumor-Associated Antigens: Recognition of Naturally Processed Epitopes Correlates with HLA-A 0201-Binding Affinity", Journal of Immunology, pp. 787-796, 2001.

De Groot, et al., "From genome to vaccine: in silico predicitions, ex vivo verification", Vaccine, pp. 4385-4395, 2001.

N. Berinstein, "Carcinoembryonic Antigen as a Target for Therapeutic Anticancer vaccines: A Review", Journal of Clinical Oncol, pp. 2197-2207, 2002.

S. Buchsbaum, et al., "Large-Scale Analysis of HLA peptides presented by HLA-Cw4", Immunogenetics, pp. 172-176, 2003.

J. Fernandez-Sueiro, et al., "Prevalence of HLA-B27 associated with ankylosing spondylitis in Galicia, Spain and subtypes of HLA-B27", Clinical Exper Reumat, pp. 465-468, 2004.

Firat, et al., "H-2 class I knockout, HLA-A2.1-transgenic mice: a versatile animal model for preclinical evaluation of antitumor immunotherapeutic strategies", Eurology Journal of Immunology, pp. 3112-3121, 1999.

Sette, et al., "The relationship between class I binding affinity and immunogenicity of potential cytotoxic T cell epitopes" The Journal of Immunolgy, pp. 5586-5592, 1994.

Sette, et al., "Nine major HLA class I supertypes account for the vast preponderance of HLA-A and -B polymorphism", Immunogentics, pp. 201-212, 1999.

Kalergis, et al., "Efficient T cell activation requires an optimal dwell-time of interaction between the TCR and the pMHC complex", Nature Immunology, pp. 229-234, 2001.

Heckerman, "A tutorial on learning Bayesian networks" Technical Report, pp. 1-5, 1995.

Greenberg, "Adoptive T cell therapy of tumors: mechanisms operative in the recognition and elimination of tumor cells", Advanced Immunology, pp. 281-355, 1991.

A. Abbas, et al., "The Major Histocompatibility Complex", Cellular and Molecular Immunology, 4th ed., ,pp. 63-73, 2000.

Rognan, D. et al. "Predicting Binding Affinities of Protein Ligands from Three-Dimensional Models: Application to Peptide Binding to Class I Major Histocompatibility Proteins", J. Med. Chem., 1999, vol. 42, pp. 4650-4658.

* cited by examiner

Figure 1B:
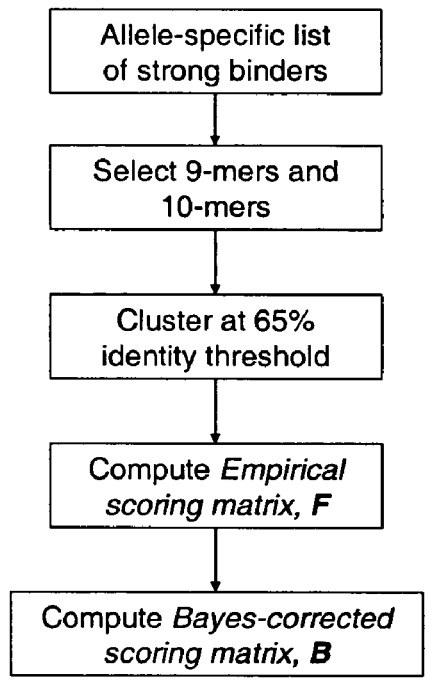

Figure 1b: Derivation of the Binding Filter

Figure 1C:
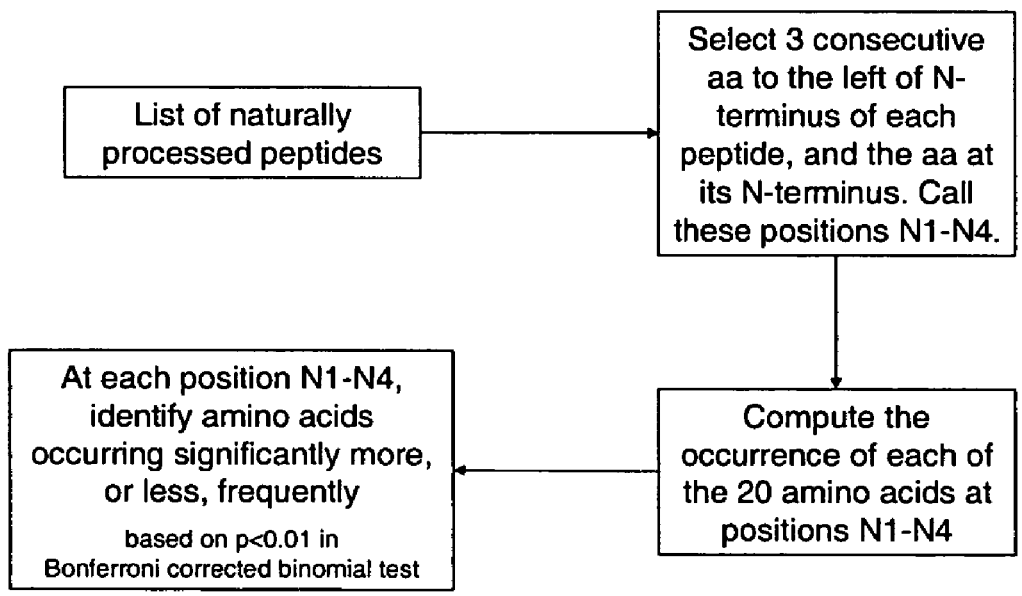

Figure 1c: Derivation of the Natural Processing Filter

Scoring a 9-mer Peptide AYCRWGLNL

Score [A Y C R W G L N L]
= B(A,1) + B(Y,2) + B(C,3) + B(R,4) + B(W,5) + B(G,6) + B(L,7) + B(N,8) + B(L,9)
= 0.17 + 2.50 - 1.10 - 0.03 - 1.10 - 0.21 - 0.38 + 0.65 + 1.65 = 2.15

| B=BSM | 1 | 2 | 3 | 4 | 5 | 6 | 7 | 8 | 9 |
|---|---|---|---|---|---|---|---|---|---|
| A | 0.17 | -0.27 | 0.17 | 0.17 | 0.72 | 0.72 | 0.48 | 0.91 | -1.10 |
| C | -1.10 | -1.10 | -1.10 | -1.10 | -1.10 | 0.90 | -1.10 | -1.10 | -1.10 |
| D | -0.04 | -1.10 | -1.10 | -0.04 | -1.10 | -1.10 | -1.10 | -1.10 | -1.10 |
| E | -1.10 | -1.10 | 0.62 | 0.30 | -0.18 | -0.18 | 0.62 | -0.18 | -0.18 |
| F | 0.69 | 1.03 | -1.10 | 0.69 | 1.29 | -1.10 | -1.10 | -1.10 | -1.10 |
| G | -1.10 | -0.21 | -0.21 | 0.26 | 0.57 | -0.21 | 0.26 | 0.26 | -1.10 |
| H | -1.10 | -1.10 | 0.59 | 0.59 | -1.10 | -1.10 | -1.10 | -1.10 | -1.10 |
| I | 0.38 | 0.38 | 1.31 | -1.10 | 0.38 | -0.11 | -1.10 | -1.10 | -0.11 |
| K | -0.11 | -1.10 | -1.10 | 0.38 | -1.10 | 0.70 | -0.11 | -0.11 | -0.11 |
| L | 0.03 | -1.10 | -0.38 | -1.10 | 0.03 | -1.10 | -0.38 | 0.54 | 1.65 |
| M | 0.55 | -1.10 | -1.10 | -1.10 | 1.51 | -1.10 | -1.10 | -1.10 | -1.10 |
| N | -1.10 | -1.10 | -1.10 | 0.65 | 1.25 | -1.10 | 0.11 | 0.65 | -1.10 |
| P | -1.10 | 0.02 | 0.54 | 0.02 | -1.10 | 0.54 | 0.02 | -1.10 | -1.10 |
| Q | -1.10 | -1.10 | 0.71 | 0.17 | -1.10 | 0.17 | 0.17 | 1.06 | -1.10 |
| R | 0.80 | -0.03 | -1.10 | -0.03 | -1.10 | 0.47 | -1.10 | -0.03 | -1.10 |
| S | 1.01 | -1.10 | -0.20 | -1.10 | -0.20 | -1.10 | 0.58 | -0.20 | -1.10 |
| T | -0.06 | -1.10 | -1.10 | 0.44 | -0.06 | 0.44 | 1.22 | 0.77 | -0.06 |
| V | -0.19 | -1.10 | 0.28 | 0.28 | 1.04 | -0.19 | -1.10 | -1.10 | 0.28 |
| W | -1.10 | -1.10 | -1.10 | -1.10 | -1.10 | -1.10 | -1.10 | -1.10 | -1.10 |
| Y | 0.91 | 2.50 | 0.34 | 0.34 | 0.34 | 0.91 | -1.10 | -1.10 | -1.10 |

Fig 3 (a) Scoring a 9mer peptide;

FIG. 3A

Scoring a 10-mer Peptide AYCRWTGLNL

Score [A Y C R W T G L N L]
= B(A,1) + B(Y,2) + B(C,3) + B(R,4) + {B(W,5)+B(T,5)}/2 + B(G,6) + B(L,7) + B(N,8) + B(L,9)
= 0.17 + 2.50 - 1.10 - 0.03 + {-1.10 - 0.06}/2 - 0.21 - 0.38 + 0.65 + 1.65 = 2.67

| B=BSM | 1 | 2 | 3 | 4 | 5 | 6 | 7 | 8 | 9 |
|---|---|---|---|---|---|---|---|---|---|
| A | 0.17 | -0.27 | 0.17 | 0.17 | 0.72 | 0.72 | 0.48 | 0.91 | -1.10 |
| C | -1.10 | -1.10 | -1.10 | -1.10 | -1.10 | 0.90 | -1.10 | -1.10 | -1.10 |
| D | -0.04 | -1.10 | -1.10 | -0.04 | -1.10 | -1.10 | -1.10 | -1.10 | -1.10 |
| E | -1.10 | -1.10 | 0.62 | 0.30 | -0.18 | -0.18 | 0.62 | -0.18 | -0.18 |
| F | 0.69 | 1.03 | -1.10 | 0.69 | 1.29 | -1.10 | -1.10 | -1.10 | -1.10 |
| G | -1.10 | -0.21 | -0.21 | 0.26 | 0.57 | -0.21 | 0.26 | 0.26 | -1.10 |
| H | -1.10 | -1.10 | 0.59 | 0.59 | -1.10 | -1.10 | -1.10 | -1.10 | -1.10 |
| I | 0.38 | 0.38 | 1.31 | -1.10 | 0.38 | -0.11 | -1.10 | -1.10 | -0.11 |
| K | -0.11 | -1.10 | -1.10 | 0.38 | -1.10 | 0.70 | -0.11 | -0.11 | -0.11 |
| L | 0.03 | -1.10 | -0.38 | -1.10 | 0.03 | -1.10 | -0.38 | 0.54 | 1.65 |
| M | 0.55 | -1.10 | -1.10 | -1.10 | 1.51 | -1.10 | -1.10 | -1.10 | -1.10 |
| N | -1.10 | -1.10 | -1.10 | 0.65 | 1.25 | -1.10 | 0.11 | 0.65 | -1.10 |
| P | -1.10 | 0.02 | 0.54 | 0.02 | -1.10 | 0.54 | 0.02 | -1.10 | -1.10 |
| Q | -1.10 | -1.10 | 0.71 | 0.17 | -1.10 | 0.17 | 0.17 | 1.06 | -1.10 |
| R | 0.80 | -0.03 | -1.10 | -0.03 | -1.10 | 0.47 | -1.10 | -0.03 | -1.10 |
| S | 1.01 | -1.10 | -0.20 | -1.10 | -0.20 | -1.10 | 0.58 | -0.20 | -1.10 |
| T | -0.06 | -1.10 | -1.10 | 0.44 | -0.06 | 0.44 | 1.22 | 0.77 | -0.06 |
| V | -0.19 | -1.10 | 0.28 | 0.28 | 1.04 | -0.19 | -1.10 | -1.10 | 0.28 |
| W | -1.10 | -1.10 | -1.10 | -1.10 | -1.10 | -1.10 | -1.10 | -1.10 | -1.10 |
| Y | 0.91 | 2.50 | 0.34 | 0.34 | 0.34 | 0.91 | -1.10 | -1.10 | -1.10 |

(b) Scoring a 10mer peptide

FIG. 3B

SEQUENCE LISTING

```
<160> NUMBER OF SEQ ID NOS: 107

<210> SEQ ID NO 1
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 1

Ala Pro His Phe Met Pro Thr Asn Leu
 1               5

<210> SEQ ID NO 2
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 2

Asp Tyr Glu Glu Leu Arg Glu Gln Leu
 1               5

<210> SEQ ID NO 3
```

```
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 3

Phe Ala Pro Gly Asn Tyr Pro Ala Leu
 1               5

<210> SEQ ID NO 4
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 4

Phe Tyr Ile Gln Met Cys Thr Glu Leu
 1               5

<210> SEQ ID NO 5
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 5

Ile Phe Ile Gly Val Gly Ala Leu Leu
 1               5

<210> SEQ ID NO 6
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 6

Ile Tyr Ser Thr Val Ala Ser Ser Leu
 1               5

<210> SEQ ID NO 7
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 7

Lys Tyr Gln Ala Val Thr Thr Thr Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 8

Leu Arg Gly Tyr Val Tyr Gln Gly Leu
 1               5

<210> SEQ ID NO 9
<211> LENGTH: 9
```

-continued

```
<212> TYPE: PRT
<213> ORGANISM: Artificial Sequence
<220> FEATURE:
<223> OTHER INFORMATION: Peptide, H-2Kd Strong Binder

<400> SEQUENCE: 9

Leu Tyr Glu Lys Val Lys Ser Gln Leu
 1               5

<210> SEQ ID NO 10
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 10

Arg Gly Tyr Val Tyr Gln Gly Leu Lys
 1               5

<210> SEQ ID NO 11
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 11

Ser Phe Ala Val Ala Thr Thr Ala Leu
 1               5

<210> SEQ ID NO 12
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 12

Ser Ile Ile Asn Phe Glu Lys Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 13

Ser Tyr Glu Thr Phe Ile Ser Arg Leu
 1               5

<210> SEQ ID NO 14
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 14

Ser Tyr Ile Pro Ala Ala Glu Lys Ile
 1               5

<210> SEQ ID NO 15
<211> LENGTH: 9
<212> TYPE: PRT
```

```
<213> ORGANISM: Artificial Sequence
<220> FEATURE:
<223> OTHER INFORMATION: Peptide, H-2Kd Strong Binder

<400> SEQUENCE: 15

Ser Tyr Ile Pro Ile Ala Glu Lys Ile
  1               5

<210> SEQ ID NO 16
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 16

Ser Tyr Ile Pro Leu Ala Glu Lys Ile
  1               5

<210> SEQ ID NO 17
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 17

Ser Tyr Ile Pro Asn Ala Glu Lys Ile
  1               5

<210> SEQ ID NO 18
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 18

Ser Tyr Val Pro Ser Ala Glu Gln Ile
  1               5

<210> SEQ ID NO 19
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 19

Thr Tyr Gln Arg Ala Arg Ala Leu Val
  1               5

<210> SEQ ID NO 20
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 20

Thr Tyr Gln Arg Asn Arg Ala Leu Val
  1               5

<210> SEQ ID NO 21
<211> LENGTH: 9
<212> TYPE: PRT
<213> ORGANISM: Artificial Sequence
```

```
<220> FEATURE:
<223> OTHER INFORMATION: Peptide, H-2Kd Strong Binder

<400> SEQUENCE: 21

Thr Tyr Gln Arg Thr Arg Ala Leu Val
 1               5

<210> SEQ ID NO 22
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 22

Val Tyr Val Asp Gly Ala Asn Gly Val
 1               5

<210> SEQ ID NO 23
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 23

Tyr Pro Ala Phe Met Pro Thr Asn Leu
 1               5

<210> SEQ ID NO 24
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 24

Tyr Pro His Phe Met Pro Thr Ala Leu
 1               5

<210> SEQ ID NO 25
<211> LENGTH: 9
<212> TYPE: PRT
<213> ORGANISM: Artificial Sequence
<220> FEATURE:
<223> OTHER INFORMATION: Peptide, H-2Kd Strong Binder

<400> SEQUENCE: 25

Tyr Pro His Phe Met Pro Thr Asn Leu
 1               5

<210> SEQ ID NO 26
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 26

Ala Tyr Leu Glu Asn Gly Lys Glu Thr Leu
 1               5                   10

<210> SEQ ID NO 27
<211> LENGTH: 10
<212> TYPE: PRT
<213> ORGANISM: Artificial Sequence
<220> FEATURE:
```

-continued

<223> OTHER INFORMATION: Peptide, H-2Kd Strong Binder

<400> SEQUENCE: 27

Met Tyr Pro His Phe Met Pro Thr Asn Leu
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 28

Arg Tyr Leu Ala Asn Gly Lys Glu Thr Leu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 29

Arg Tyr Leu Glu Ala Gly Lys Glu Thr Leu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 30

Arg Tyr Leu Glu Asn Ala Lys Glu Thr Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 31

Arg Tyr Leu Glu Asn Gly Ala Glu Thr Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 32

Arg Tyr Leu Glu Asn Gly Lys Ala Thr Leu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Peptide, H-2Kd Strong Binder -continued

```
<400> SEQUENCE: 33

Arg Tyr Leu Glu Asn Gly Lys Glu Ala Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 34

Arg Tyr Leu Glu Asn Gly Lys Glu Thr Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 35

Arg Tyr Leu Lys Ala Gly Lys Glu Thr Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 36

Arg Tyr Pro His Phe Met Pro Thr Asn Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 37

Ser Ile Ile Asn Phe Glu Lys Leu Thr Glu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Peptide, H-2Kd Strong Binder

<400> SEQUENCE: 38

Tyr Phe Ile Phe Ile Gly Val Gly Ala Leu
1               5                   10

<210> SEQ ID NO 39
<211> LENGTH: 9
<212> TYPE: PRT
<213> ORGANISM: Artificial Sequence
<220> FEATURE:
<223> OTHER INFORMATION: A2-restricted epitope from HCV
```

```
<400> SEQUENCE: 39

Asp Leu Met Gly Tyr Ile Pro Leu Val
 1               5

<210> SEQ ID NO 40
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 40

Tyr Leu Val Ala Tyr Gln Ala Thr Val
 1               5

<210> SEQ ID NO 41
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 41

Ile Leu Ala Gly Tyr Gly Ala Gly Val
 1               5

<210> SEQ ID NO 42
<211> LENGTH: 10
<212> TYPE: PRT
<213> ORGANISM: Artificial Sequence
<220> FEATURE:
<223> OTHER INFORMATION: A2-restricted epitope from HCV

<400> SEQUENCE: 42

Tyr Leu Leu Pro Arg Arg Gly Pro Arg Leu
 1               5                  10

<210> SEQ ID NO 43
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 43

Val Leu Val Gly Gly Val Leu Ala Ala
 1               5

<210> SEQ ID NO 44
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 44

Phe Leu Leu Leu Ala Asp Ala Arg Val
 1               5

<210> SEQ ID NO 45
<211> LENGTH: 10
<212> TYPE: PRT
<213> ORGANISM: Artificial Sequence
<220> FEATURE:
<223> OTHER INFORMATION: A2-restricted epitope from HCV

<400> SEQUENCE: 45
```

```
Leu Leu Phe Asn Ile Leu Gly Gly Trp Val
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: A2-restricted epitope from HCV

<400> SEQUENCE: 46

Arg Leu Ile Val Phe Pro Asp Leu Gly Val
 1               5                  10

<210> SEQ ID NO 47
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 47

His Met Trp Asn Phe Ile Ser Gly Ile
 1               5

<210> SEQ ID NO 48
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 48

Tyr Leu Val Thr Arg His Ala Asp Val
 1               5

<210> SEQ ID NO 49
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 49

Leu Leu Phe Leu Leu Leu Ala Asp Ala
 1               5

<210> SEQ ID NO 50
<211> LENGTH: 9
<212> TYPE: PRT
<213> ORGANISM: Artificial Sequence
<220> FEATURE:
<223> OTHER INFORMATION: A2-restricted epitope from HCV

<400> SEQUENCE: 50

Trp Met Asn Arg Leu Ile Ala Phe Ala
 1               5

<210> SEQ ID NO 51
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 51
```

```
Ser Leu Tyr Asn Thr Val Ala Thr Leu
 1               5
```

<210> SEQ ID NO 52
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 52

```
Lys Leu Thr Pro Leu Cys Val Ser Leu
 1               5
```

<210> SEQ ID NO 53
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 53

```
Val Leu Ala Glu Ala Met Ser Gln Val
 1               5
```

<210> SEQ ID NO 54
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 54

```
Ile Leu Lys Glu Pro Val His Gly Val
 1               5
```

<210> SEQ ID NO 55
<211> LENGTH: 10
<212> TYPE: PRT
<213> ORGANISM: Artificial Sequence
<220> FEATURE:
<223> OTHER INFORMATION: A2-restricted epitope from HIV-1

<400> SEQUENCE: 55

```
Ser Leu Leu Asn Ala Thr Ala Ile Ala Val
 1               5                  10
```

<210> SEQ ID NO 56
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 56

```
Arg Leu Arg Asp Leu Leu Leu Ile Val
 1               5
```

<210> SEQ ID NO 57
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 57

```
Leu Leu Trp Lys Gly Glu Gly Ala Val
```

<210> SEQ ID NO 58
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 58

Ala Leu Val Glu Ile Cys Thr Glu Met
 1               5

<210> SEQ ID NO 59
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 59

Leu Leu Asn Ala Thr Ala Ile Ala Val
 1               5

<210> SEQ ID NO 60
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 60

Gln Met His Glu Asp Ile Ile Ser Leu
 1               5

<210> SEQ ID NO 61
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 61

Ala Ile Ile Arg Ile Leu Gln Gln Leu
 1               5

<210> SEQ ID NO 62
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 62

Arg Ile Leu Gln Gln Leu Leu Phe Ile
 1               5

<210> SEQ ID NO 63
<211> LENGTH: 10
<212> TYPE: PRT
<213> ORGANISM: Artificial Sequence
<220> FEATURE:
<223> OTHER INFORMATION: A2-restricted epitope from HIV-1

<400> SEQUENCE: 63

Glu Ile Leu Lys Glu Pro Val His Gly Val
 1               5                   10

<210> SEQ ID NO 64
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 64

Leu Val Gly Pro Thr Pro Val Asn Ile
1               5

<210> SEQ ID NO 65
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 65

Val Ile Tyr Gln Tyr Met Asp Asp Leu
1               5

<210> SEQ ID NO 66
<211> LENGTH: 9
<212> TYPE: PRT
<213> ORGANISM: Artificial Sequence
<220> FEATURE:
<223> OTHER INFORMATION: A2-restricted epitope from HIV-1

<400> SEQUENCE: 66

Tyr Gln Tyr Met Asp Asp Leu Tyr Val
1               5

<210> SEQ ID NO 67
<211> LENGTH: 10
<212> TYPE: PRT
<213> ORGANISM: Artificial Sequence
<220> FEATURE:
<223> OTHER INFORMATION: A2-restricted epitope from HIV-1

<400> SEQUENCE: 67

Arg Gly Pro Gly Arg Ala Phe Val Thr Ile
1               5                   10

<210> SEQ ID NO 68
<211> LENGTH: 10
<212> TYPE: PRT
<213> ORGANISM: Artificial Sequence
<220> FEATURE:
<223> OTHER INFORMATION: A2-restricted epitope from HIV-1

<400> SEQUENCE: 68

Ile Tyr Gln Tyr Met Asp Asp Leu Tyr Val
1               5                   10

<210> SEQ ID NO 69
<211> LENGTH: 10
<212> TYPE: PRT
<213> ORGANISM: Artificial Sequence
<220> FEATURE:
<223> OTHER INFORMATION: immunogenic analog of PSA epitope

<400> SEQUENCE: 69

Leu Val His Pro Gln Trp Val Leu Thr Val
1               5                   10

<210> SEQ ID NO 70
<211> LENGTH: 261
<212> TYPE: PRT
<213> ORGANISM: Homo Sapiens

<400> SEQUENCE: 70

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
    35                  40                  45

Val Cys Gly Gly Val Leu Val His Pro Gln Trp Val Leu Thr Ala Ala
50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 71
<211> LENGTH: 10
<212> TYPE: PRT
<213> ORGANISM: Artificial Sequence
<220> FEATURE:
<223> OTHER INFORMATION: tryptase delta 63 peptide

<400> SEQUENCE: 71

Leu Ile His Pro Gln Trp Val Leu Thr Ala
1               5                   10

<210> SEQ ID NO 72
<211> LENGTH: 235
<212> TYPE: PRT
<213> ORGANISM: Homo Sapiens

<400> SEQUENCE: 72

```
Met Leu Ser Leu Leu Leu Leu Ala Leu Pro Val Leu Ala Ser Pro Ala
 1               5                  10                  15

Tyr Val Ala Pro Ala Pro Gly Gln Ala Leu Gln Gln Thr Gly Ile Val
             20                  25                  30

Gly Gly Gln Glu Ala Pro Arg Ser Lys Trp Pro Trp Gln Val Ser Leu
         35                  40                  45

Arg Val Arg Gly Pro Tyr Trp Met His Phe Cys Gly Gly Ser Leu Ile
 50                  55                  60

His Pro Gln Trp Val Leu Thr Ala Ala His Cys Val Glu Pro Asp Ile
65                  70                  75                  80

Lys Asp Leu Ala Ala Leu Arg Val Gln Leu Arg Glu Gln His Leu Tyr
                 85                  90                  95

Tyr Gln Asp Gln Leu Leu Pro Val Ser Arg Ile Ile Val His Pro Gln
            100                 105                 110

Phe Tyr Ile Ile Gln Thr Gly Ala Asp Ile Ala Leu Leu Glu Leu Glu
            115                 120                 125

Glu Pro Val Asn Ile Ser Ser His Ile His Thr Val Thr Leu Pro Pro
130                 135                 140

Ala Ser Glu Thr Phe Pro Pro Gly Met Pro Cys Trp Val Thr Gly Trp
145                 150                 155                 160

Gly Asp Val Asp Asn Asn Val His Leu Pro Pro Tyr Pro Leu Lys
                165                 170                 175

Glu Val Glu Val Pro Val Val Glu Asn His Leu Cys Asn Ala Glu Tyr
            180                 185                 190

His Thr Gly Leu His Thr Gly His Ser Phe Gln Ile Val Arg Asp Asp
        195                 200                 205

Met Leu Cys Ala Gly Ser Glu Asn His Asp Ser Cys Gln Gly Asp Ser
    210                 215                 220

Gly Gly Pro Leu Val Cys Lys Val Asn Gly Thr
225                 230                 235

<210> SEQ ID NO 73
<211> LENGTH: 9
<212> TYPE: PRT
<213> ORGANISM: Artificial Sequence
<220> FEATURE:
<223> OTHER INFORMATION: EBNA 3C.881 peptide from Epstein-Barr virus

<400> SEQUENCE: 73

Gln Pro Arg Ala Pro Ile Arg Pro Ile
 1               5

<210> SEQ ID NO 74
<211> LENGTH: 9
<212> TYPE: PRT
<213> ORGANISM: Artificial Sequence
<220> FEATURE:
<223> OTHER INFORMATION: EBNA 3A.379 peptide from Epstien Barr virus

<400> SEQUENCE: 74

Arg Pro Pro Ile Phe Ile Arg Arg Leu
 1               5

<210> SEQ ID NO 75
<211> LENGTH: 261
<212> TYPE: PRT
<213> ORGANISM: Homo Sapiens

<400> SEQUENCE: 75
```

```
Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
 50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
               100                 105                 110

Pro Gly Asp Asp Ser Ser His Asp Leu Met Leu Leu Arg Leu Ser Glu
               115                 120                 125

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
            195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
                260

<210> SEQ ID NO 76
<211> LENGTH: 10
<212> TYPE: PRT
<213> ORGANISM: Artificial Sequence
<220> FEATURE:
<223> OTHER INFORMATION: Prostate specific antigen (PSA.165) peptide

<400> SEQUENCE: 76

Phe Leu Thr Pro Lys Lys Leu Gln Cys Val
 1               5                  10

<210> SEQ ID NO 77
<211> LENGTH: 9
<212> TYPE: PRT
<213> ORGANISM: Artificial Sequence
<220> FEATURE:
<223> OTHER INFORMATION: Prostate specific antigen peptide

<400> SEQUENCE: 77

Lys Leu Gln Cys Val Asp Leu His Val
 1               5
```

```
<210> SEQ ID NO 78
<211> LENGTH: 10
<212> TYPE: PRT
<213> ORGANISM: Artificial Sequence
<220> FEATURE:
<223> OTHER INFORMATION: Prostate specific antigen (PSA.178) peptide

<400> SEQUENCE: 78

Val Ile Ser Asn Asp Val Cys Ala Gln Val
 1               5                  10

<210> SEQ ID NO 79
<211> LENGTH: 9
<212> TYPE: PRT
<213> ORGANISM: Artificial Sequence
<220> FEATURE:
<223> OTHER INFORMATION: Prostate specific antigen peptide

<400> SEQUENCE: 79

Val Leu Val His Pro Gln Trp Val Leu
 1               5

<210> SEQ ID NO 80
<211> LENGTH: 9
<212> TYPE: PRT
<213> ORGANISM: Artificial Sequence
<220> FEATURE:
<223> OTHER INFORMATION: Prostate specific antigen peptide

<400> SEQUENCE: 80

Phe Leu Thr Leu Ser Val Thr Trp Ile
 1               5

<210> SEQ ID NO 81
<211> LENGTH: 10
<212> TYPE: PRT
<213> ORGANISM: Artificial Sequence
<220> FEATURE:
<223> OTHER INFORMATION: Prostate specific antigen peptide

<400> SEQUENCE: 81

Val Leu Val Ala Ser Arg Gly Arg Ala Val
 1               5                  10

<210> SEQ ID NO 82
<211> LENGTH: 10
<212> TYPE: PRT
<213> ORGANISM: Artificial Sequence
<220> FEATURE:
<223> OTHER INFORMATION: Prostate specific antigen (PSA.217) peptide

<400> SEQUENCE: 82

Leu Val Cys Asn Gly Val Leu Gln Gly Ile
 1               5                  10

<210> SEQ ID NO 83
<211> LENGTH: 10
<212> TYPE: PRT
<213> ORGANISM: Artificial Sequence
<220> FEATURE:
<223> OTHER INFORMATION: Prostate specific antigen (PSA.54) peptide

<400> SEQUENCE: 83

Leu Val His Pro Gln Trp Val Leu Thr Ala
 1               5                  10

<210> SEQ ID NO 84
```

```
<211> LENGTH: 9
<212> TYPE: PRT
<213> ORGANISM: Artificial Sequence
<220> FEATURE:
<223> OTHER INFORMATION: Prostate specific antigen peptide

<400> SEQUENCE: 84

Gly Val Leu Val His Pro Gln Trp Val
 1               5

<210> SEQ ID NO 85
<211> LENGTH: 10
<212> TYPE: PRT
<213> ORGANISM: Artificial Sequence
<220> FEATURE:
<223> OTHER INFORMATION: Prostate specific antigen peptide

<400> SEQUENCE: 85

Lys Leu Gln Cys Val Asp Leu His Val Ile
 1               5                  10

<210> SEQ ID NO 86
<211> LENGTH: 10
<212> TYPE: PRT
<213> ORGANISM: Artificial Sequence
<220> FEATURE:
<223> OTHER INFORMATION: PSA epitope, immunogenic analog

<400> SEQUENCE: 86

Val Leu Ser Asn Asp Val Cys Ala Gln Val
 1               5                  10

<210> SEQ ID NO 87
<211> LENGTH: 9
<212> TYPE: PRT
<213> ORGANISM: Artificial Sequence
<220> FEATURE:
<223> OTHER INFORMATION: PSA epitope, immunogenic analog

<400> SEQUENCE: 87

Phe Leu Thr Leu Ser Val Thr Trp Val
 1               5

<210> SEQ ID NO 88
<211> LENGTH: 10
<212> TYPE: PRT
<213> ORGANISM: Artificial Sequence
<220> FEATURE:
<223> OTHER INFORMATION: PSA epitope, immunogenic analog

<400> SEQUENCE: 88

Lys Leu Gln Cys Val Asp Leu His Val Val
 1               5                  10

<210> SEQ ID NO 89
<211> LENGTH: 261
<212> TYPE: PRT
<213> ORGANISM: Artificial Sequence
<220> FEATURE:
<223> OTHER INFORMATION: PSA, immunoenhanced protein

<400> SEQUENCE: 89

Met Trp Val Pro Val Val Phe Leu Thr Leu Ser Val Thr Trp Val Gly
 1               5                  10                  15

Ala Ala Pro Leu Ile Leu Ser Arg Ile Val Gly Gly Trp Glu Cys Glu
                20                  25                  30
```

```
Lys His Ser Gln Pro Trp Gln Val Leu Val Ala Ser Arg Gly Arg Ala
        35                  40                  45

Val Cys Gly Gly Leu Leu Val His Pro Gln Trp Val Val Thr Val Ala
 50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
                100                 105                 110

Pro Gly Asp Asp Ser Ser His Asp Leu Met Leu Leu Arg Leu Ser Glu
                115                 120                 125

Pro Ala Glu Leu Thr Asp Ala Val Lys Val Met Asp Leu Pro Thr Gln
                130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Leu Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
                195                 200                 205

Cys Ser Gly Asp Ser Gly Gly Pro Leu Leu Cys Asn Gly Val Leu Gln
                210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 90
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 90

Ala Ile Ile Asn Phe Glu Lys Leu
 1               5

<210> SEQ ID NO 91
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 91

Arg Gly Tyr Val Tyr Gln Gly Leu
 1               5

<210> SEQ ID NO 92
<211> LENGTH: 8
<212> TYPE: PRT
<213> ORGANISM: Artificial Sequence
<220> FEATURE:
<223> OTHER INFORMATION: Peptide, H-2Kd Strong Binder
```

```
<400> SEQUENCE: 92

Ser Ala Ile Asn Phe Glu Lys Leu
 1               5

<210> SEQ ID NO 93
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 93

Ser Ile Ile Ala Phe Glu Lys Leu
 1               5

<210> SEQ ID NO 94
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 94

Ser Ile Ile Asn Phe Ala Lys Leu
 1               5

<210> SEQ ID NO 95
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 95

Ser Ile Ile Asn Phe Glu Ala Leu
 1               5

<210> SEQ ID NO 96
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 96

Ser Ile Ile Asn Phe Glu Lys Leu
 1               5

<210> SEQ ID NO 97
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 97

Tyr Ile Pro Ala Ala Glu Lys Ile
 1               5

<210> SEQ ID NO 98
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 98
```

Tyr Ile Pro Leu Ala Glu Lys Ile
1               5

<210> SEQ ID NO 99
<211> LENGTH: 8
<212> TYPE: PRT
<213> ORGANISM: Artificial Sequence
<220> FEATURE:
<223> OTHER INFORMATION: Peptide, H-2Kd Strong Binder

<400> SEQUENCE: 99

Tyr Ile Pro Asn Ala Glu Lys Ile
1               5

<210> SEQ ID NO 100
<211> LENGTH: 11
<212> TYPE: PRT
<213> ORGANISM: Artificial Sequence
<220> FEATURE:
<223> OTHER INFORMATION: Peptide, H-2Kd Strong Binder

<400> SEQUENCE: 100

Thr Tyr Gln Arg Thr Arg Ala Leu Val Thr Gly
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Peptide, H-2Kd Strong Binder

<400> SEQUENCE: 101

Thr Tyr Gln Arg Thr Arg Ala Leu Val Thr Thr Gly
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Peptide, H-2Kd Strong Binder

<400> SEQUENCE: 102

Ile Ser Thr Gln Asn His Arg Ala Leu Asp Leu Val Ala
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Completely synthetic peptide, random sequence

<400> SEQUENCE: 103

Ala Tyr Cys Arg Trp Gly Leu Asn Leu
1               5

<210> SEQ ID NO 104
<211> LENGTH: 10
<212> TYPE: PRT
<213> ORGANISM: Artificial Sequence
<220> FEATURE:
<223> OTHER INFORMATION: Completely synthetic peptide, random sequence

<400> SEQUENCE: 104

```
Ala Tyr Cys Arg Trp Thr Gly Leu Asn Leu
1               5                   10

<210> SEQ ID NO 105
<211> LENGTH: 9
<212> TYPE: PRT
<213> ORGANISM: Artificial Sequence
<220> FEATURE:
<223> OTHER INFORMATION: PSA epitope, immunogenic analog

<400> SEQUENCE: 105

Val Leu Val His Pro Gln Trp Val Val
1               5

<210> SEQ ID NO 106
<211> LENGTH: 10
<212> TYPE: PRT
<213> ORGANISM: Artificial Sequence
<220> FEATURE:
<223> OTHER INFORMATION: PSA epitope, immunogenic analog

<400> SEQUENCE: 106

Leu Leu Cys Asn Gly Val Leu Gln Gly Ile
1               5                   10

<210> SEQ ID NO 107
<211> LENGTH: 9
<212> TYPE: PRT
<213> ORGANISM: Artificial Sequence
<220> FEATURE:
<223> OTHER INFORMATION: PSA epitope, immunogenic analog

<400> SEQUENCE: 107

Gly Leu Leu Val His Pro Gln Trp Val
1               5
```

SYSTEM AND METHOD FOR AUTOMATED SELECTION OF T-CELL EPITOPES

CROSS-REFERENCE TO RELATED APPLICATIONS

This application claims the benefit of U.S. Provisional Application No. 60/680,323, filed May 12, 2005, herein incorporated by reference.

FIELD OF THE INVENTION

The present invention relates to a field of bioinformatics referred to as immunoinformatics. More specifically, the invention provides a data processing system and methodology for predicting and/or optimizing the binding affinities of peptides derived from immunologically relevant antigens, to molecules of the major histocompatibility complex (MHC).

REFERENCE TO SEQUENCE LISTING SUBMITTED ELECTRONICALLY

The sequence listing of the present application is submitted electronically via EFS-Web as an ASCII formatted sequence listing with a file name "IRRIFD0015YPDBUSPCD_SEQLIST_06MAY2010.TXT," creation date of May 6, 2010, and a size of 29 KB. This sequence listing submitted via EFS-Web is part of the specification and is herein incorporated by reference in its entirety.

BACKGROUND OF THE INVENTION

Epitope vaccines provide a potential means for the treatment and prevention of infectious diseases, and for promoting the destruction of cancerous cells by an individual's immune system. It is well established that $CD8^+$ cytotoxic T lymphocytes (CTL) play a crucial role in the eradication of infectious diseases and tumor cells by the mammalian immune system. MHC class I restricted epitope vaccines have been shown to confer protection in animal models, and it is widely believed that the development of epitope vaccines encoding human HLA-restricted CTL epitopes capable of conferring broad, effective, and non-ethnically biased population coverage is feasible.

Epitope-based vaccines offer a number of advantageous features, including the features that: they represent potent immunogens which can be constructed in a manner designed to target multiple conserved epitopes in a rapidly mutating pathogen (such as HCV or HIV), they can induce immune responses to subdominant epitopes (for example against a tumor associated antigen in a situation in which there is tolerance to a dominant epitope), they can be analogued to break tolerance or increase immunogenicity, and their use minimizes safety risks associated with the use of intact proteins or attenuated pathogens.

The immune system functions to discriminate molecules endogenous to an organism ("self" molecules) from material exogenous or foreign to the organism ("non-self" molecules). The human immune system recognizes antigens produced by its own cells, including pathogenic proteins (produced as a consequence of infection with an intracellular bacterial, viral or parasitic pathogen), and aberrant self-proteins (mutated self proteins expressed as a consequence of a cancerous process) by means of the major histocompatibility complex (MHC). More specifically, MHC molecule/MHC peptide complexes interact with antigen-specific T-cell receptors (TCR) to provide a context for the recognition of antigens by effector T-cells. Activation of effector T-cells triggers an immune response.

MHC/peptide complexes are displayed on the surface of antigen-presenting cells (APC), and most often consist of short protein segments (i.e., T-cell Epitopes) held in a pocket-like groove of an MHC class I or class II molecules. Typically, MHC class I ligands comprise 8-11 amino acids and are derived from endogenously expressed proteins which are degraded by cytosolic proteases. MHC class I molecules show preferential restriction to CD8+ cells. (A. Abbas et. al., Cellular and Molecular Immunology, 4th ed. 2000, Chapter 4, pp 63-73). In order for a T-cell epitope to be highly immunogenic it must not only promote stable enough TCR binding for activation to occur, but the TCR must also have a high enough off-rate that multiple TCR molecules can interact sequentially with the same peptide-MHC complex (A. Kalergis et al., *Nature Immunol* 2001, 2:229-234).

The tripartite interaction of the: 1) T-cell Receptor (TCR) with, 2) a major histocompatibility complex (MHC) molecule, or human leukocyte antigen (HLA) molecule, bound to, 3) an antigenic peptide derived from a pathogenic agent or cancerous cell, is crucial for eliciting a specific immune response against a cell expressing the immunologically relevant antigen. Recognition of a MHC class I-peptide complex by a TCR found on the surface of CD8+ cytotoxic T lymphocyte (CTL) activates an immune response which ultimately results in destruction (e.g., apoptosis) of the peptide-presenting cell.

The pathway from protein sequence analysis to vaccine development requires the development of binding assays for testing the affinity of candidate epitopes to particular MHC molecules, the establishment of in vitro assays suitable for evaluating the T-cell response, and ultimately in vivo testing of the immunogenicity and efficacy of a particular immunogenic composition. T-cell epitopes can be empirically determined by numerous experimental approaches, including peptide mapping, screening of combinatorial peptide libraries, production and screening of expression libraries derived from tissues of interest, or elution and sequencing of naturally occurring peptides from MHC molecules. Depending upon the nature of the target protein, empirical determination can be too expensive in terms of time, labor, and resources to be practical. Thus, there is considerable incentive to utilize data-driven computational methods, as a high throughput alternative to empirical work.

Although there are a wide variety of sequence-based methods for T-cell epitope identification, there is an unmet need for data processing systems which provide analytical methods for the identification and/or modification of known, or predicted, T-cell epitopes. In particular there is a need to identify modifications that confer T-cell epitopes with the ability to elicit stronger cellular immune responses because of more efficient antigen processing and/or presentation.

SUMMARY OF THE INVENTION

The present invention discloses a computational tool for T-cell epitope prediction and immunoenhancement which utilizes the informational content of amino acid sequences of foreign or self origin to model the binding preferences of individual MHC alleles. More specifically, the invention provides an epitope identification algorithm for MHC class I epitope prediction and/or optimization. Use of the disclosed data processing system allows an artisan to identify and rank amino acid sequences derived from an immunologically relevant antigen, based on their predicted ability to bind to a MHC class I allele. The invention described herein can be implemented using computer hardware or software, or a combination of both. Utilization of the disclosed computational methods for the automated selection and/or optimization of T-cell epitopes will facilitate the design and development of improved immunodiagnostics and immunotherapeutics (e.g., immunogenic compositions or vaccines).

In one aspect, the invention provides an epitope selection matrix, or a binding filter, which can be use to score and rank candidate T-cell epitopes, based on their predicted abilities to bind to an HLA class I allele. The invention also provides a natural processing filter, a self-similarity filter, and an immunogenic enhancement filter, any or all, of which can be used alone or in combination with the disclosed binding filter. In particular embodiments, the natural processing filter, the self-similarity filter, or the immunogenic enhancement filter can be used as individual computational tools to optimize known T-cell epitopes identified by alternative methodology. T-cell epitopes identified and/or optimized using the disclosed methodology and filters can be used as part of a gene-, protein-, vector-, or cell-based vaccine to treat or prevent an infectious disease or cancer, or as part of an immunodiagnostic assay designed to measure in vivo cellular immune responses induced by the administration of an immunogenic composition comprising one or more T-cell epitopes derived from a target antigen.

Therapeutic use of epitope vaccines and immunogenic compositions requires the identification of peptide sequences (i.e., T-cell epitopes) which stimulate a subject's immune system to mount an immune response against their own infected or transformed cells. Consistent with this goal, one aspect of the invention provides a binding filter which can be used as the basis of a computer assisted method for predicting (e.g., identifying) T-cell epitopes that are likely to bind to an MHC class I allele of interest. Briefly, the selection process comprises the steps of selecting an MHC allele of interest, collecting and curating a training set which comprises peptide sequences which are known to bind to the MHC allele (i.e., MHC peptides), assigning the training peptides to clusters based on sequence similarity, determining an empirical binding score matrix, and calculating a Bayes-corrected scoring matrix. The scoring matrix derived from the informational content of the training set peptides is used as an epitope selection matrix to score and rank candidate T-cell epitopes derived empirically or using an in silico algorithm from a target protein.

The disclosed epitope selection matrix (binding filter) can be used to identify T-cell epitopes in a target protein which is derived from a foreign (e.g., viral or non-viral protein) or from a self antigen. Accordingly, one aspect of the invention provides a method for predicting whether a naturally occurring peptide sequence derived from a target protein will bind to an MHC allele of interest. More specifically, the invention provides a method for identifying putative T-cell epitopes, from a set of candidate epitopes representing all possible 9-mer and 10-mer peptide sequences, of a target protein which are predicted to bind to an MHC molecule of interest. Briefly, the method involves computing a Bayes-corrected scoring matrix from the binding information derived from clusters MHC peptides known to bind to the MHC allele of interest and using the resulting matrix to determine binding scores for candidate T-cell epitopes.

In an alternative aspect, the invention provides a method for predicting whether an analogued synthetic peptide sequence, such as an anchor-modified immunogenic analog, is likely to induce a stronger immune response, than a parental (naturally occurring, or modeled) peptide sequence from which it is derived. Briefly, evaluation of analogued sequences involves using a binding filter to calculate a binding score for a proposed optimized sequence (i.e., analog) and comparing the score obtained for the analog to the score determined for the parental sequence as described in Example 8.

An alternative aspect of the invention provides a natural processing filter which can be used to identify and reject candidate T-cell epitopes which are unlikely to be presented to T-cells due to impaired cellular processing. Because antigen presentation in the context of an HLA molecule is a prerequisite for recognition by T-cells, peptides possessing one or more of the identified interfering motifs are presumed to be suboptimal candidates for inclusion in an epitope-based vaccine. The natural processing filter disclosed herein is utilized to analyze candidate epitopes' flanking residues for the presence of one of several amino acid motifs associated with decreased likelihood of antigen processing and/or presentation on the cell surface of antigen presentation cells (APCs). In practice, the natural processing filter allows an artisan to identify peptides which based solely on their binding scores would appear to be a good T-cell epitope candidate but which are likely to be non-immunogenic in-vivo.

The natural processing filter of the invention is implemented as a rule which rejects a candidate T-cell epitope peptide if it has a proline residue at position P1 or P1', or a leucine residue at position P1'. Thus an alternative aspect of the invention describes an analytical method for the identification of modifications in known or predicted T-cell epitopes that could confer the modified epitopes with an ability to elicit stronger cellular immune response due to more efficient processing and/or presentation to T-cells. In addition to being used as a component of the data processing system, the disclosed natural processing rule can also be used as a stand-alone filter to rank a set of candidate T-cell epitopes, identified by empirical determination or by using an alternative in silico methodology, based on the likelihood that the peptides will be efficiently processed or displayed by APCs. It is well-known that the inclusion of a self-similar peptide in its native form in an immunogenic composition may elicit an off-target autoimmune response. For example, published studies reporting T-cell-mediated destruction of melanocytes (van Elsas et al., *JEM* 1999, 190: 355-366) and pancreatic islet β-cells (Ludewig et. al., *JEM* 2000, 191: 795-804) following immunotherapy provide exemplify the consequences of administering an immunogenic composition which comprises self-similar peptides which elicit unwanted off-target immune responses in vivo.

In order to improve the specificity of immunogenic compositions that are formulated on the basis of the disclosed methodology the invention also provides a self-similarity filter. In practice, the disclosed self-similarity filter allows an investigator to eliminate candidate epitopes which are not unique to the target antigen. In particular embodiments, the self-similarity filter can optionally be used as a component of a selection process designed to identify T-cell epitopes for tumor associated antigens. Alternatively, as noted above for the natural processing filter, the self-similarity filter of the invention can be used as a stand alone filter to identify T-cell epitopes which are unique to and specific for a target antigen.

The self-similarity filter of the invention operates by identifying and flagging candidate epitopes which are identical, or highly similar, to a naturally occurring amino acid sequence present in a non-target protein. Inclusion of this filter in the algorithm allows an artisan to curate a ranked list of peptides (based on binding score) by eliminating candidate epitopes which have amino acid sequences that are similar to a non-target protein. In practice, the self-similarity filter is implemented as a rule which rejects a candidate T-cell epitope if another protein, in an appropriate database of reference sequences, contains an amino acid sequence that is either 1) identical to the amino acid sequence of the candidate T-cell epitope or 2) differs by 1 or 2 amino acids from the amino acid sequence of the candidate T-cell epitope, and the mismatches are restricted to the MHC anchor positions (positions 2 and 9/10, for most Class I alleles) which are buried within the MHC binding groove and thus do not affect T-cell recognition.

In an additional aspect the invention also provides methodology for the identification of anchor-modified immunogenic analogs which elicit enhanced immune responses relative to the immune response elicited by the naturally occurring parental amino acid sequence. The immunoenhancement filter of the invention can be used to identify amino acid substitutions of anchor residues which are likely to confer a putative T-cell epitope with the ability to elicit a stronger immune response than the unmodified naturally occurring (i.e., wild-type) peptide. In practice, the immunogenicity enhancement filter can be used to identify and evaluate amino acid modifications that can be introduced into candidate T-cell epitopes to prepare an analog that is predicted to elicit an enhanced immune response that is predicted to be cross-reactive with the response elicited by the wild-type peptide. The predicted cross-reactivity is premised on the expectation that T-cells specific for the modified peptide should recognize the wild-type peptide because of the identical amino acid residues in the TCR contact region [Keogh eta, *J. Immunol.* 2001, 167: 787-796]. Therefore, it is reasonable to assume that an analog will elicit a cross-reactive immune response. Typically, the immunoenhancement filter is used to propose modifications in candidate sequences which have been curated to exclude self-similar sequences, in order to improve binding to the HLA molecule [M. Parkhurst et al., *J Immunol* 1996, 157: 2539-2548]. The predicted binding strength of the analog can be evaluated using the above-described binding filter.

In yet another alternative aspect the invention also provides a computer-based method which can be employed to identify targets for use in in-vitro assays designed to evaluate vaccine-induced cellular immune response against pathogenic or tumor-associated proteins of interest. For example, the disclosed methodology allows investigators to rationally select peptides for use in in-vitro diagnostic assays (e.g., efficacy assays) designed to evaluate antigen-specific cellular immunity pre- and post-vaccination with an immunogenic composition comprising one or more T-cell epitopes. More specifically, the magnitude and/or functional activity of antigen-specific T-cells pre- and post-vaccination can be measured using predicted T-cell epitope(s) as probes in standard T-cell activation assays such as tetramer, ELISPOT, or ICS assays.

The references cited throughout the present disclosure are not admitted to be prior art to the claimed invention.

BRIEF DESCRIPTION OF THE DRAWINGS

FIGS. 1*a*-1*c* provide flowcharts which summarizing the processes of data selection and scoring matrix computation (FIG. 1*a*), training the binding affinity filter (FIG. 1*b*) and the natural processing filter, (FIG. 1*c*).

FIG. 2 provides a flowchart summarizing the use of the disclosed epitope identification algorithm to identify and rank candidate T-cell epitopes or analogs from an immunologically relevant antigen.

FIGS. 3*a*-3b illustrate how a binding score is calculated for a 9-mer (FIG. 3*a*) and 10-mer (FIG. 3*b*) candidate T-cell epitopes.

DETAILED DESCRIPTION OF THE INVENTION

Unless defined otherwise, technical and scientific terms used herein have the meanings commonly understood by one of ordinary skill in the art to which the present invention pertains. One skilled in the art will recognize other methods and materials similar or equivalent to those described herein, which can be used in the practice of the present teaching. It is to be understood, that the teachings presented herein are not intended to limit the methodology or processes described herein. For purposes of the present invention, the following terms are defined below.

As used herein, the terms "9-mer" and "10-mer" refer to a linear sequence of nine or ten amino acids that occur in a target antigen. It is generally understood, that a collection of sequences which includes all possible 9-mers and 10-mers present in a parent sequence, comprise sequences which overlap by eight or nine residues, respectively.

As used herein, the term "anchor residues" refer to the amino acid residues of a peptide fragment containing side chains that fit into the peptide-binding clefts of MHC molecules.

As used herein, the term "antigen" refers to any biologic or macromolecular substance that can be recognized by a T-cell or an antibody molecule.

As used herein, a "binding motif" refers to a specific pattern or combination of anchor residues within protein sequences which are correlated with the ability to bind to a specified HLA alleles or serotypes.

As used herein, the terms "major histocompatibility complex (MHC)" and "human leukocyte antigen (HLA)" are used interchangeably to refer to a locus of genes that encode proteins which present a vast variety of peptides onto the cell surface for specific recognition by a T-cell receptor. A subclass of MHC genes, called Class I MHC molecules, present peptides to $CD8^+$ T-cells.

As used herein, an "immunogen" refers to specific antigens that are capable of inducing or stimulating an immune response. Not all antigens are immunogenic.

As used herein the term "enhanced immunogenicity" refers an increased ability to activate the immune system when compared to the immune response elicited by the parental peptide. A variant peptide or analog can be said to have "increased immunogenicity" if it induces a higher level of T-cell activation relative to the level of activation induced by the parental peptide as measured in a standard in-vitro T-cell activation assay. In a preferred embodiment, the frequency of vaccination-induced epitope-specific T-cells will be increased at least 10-fold by the administration of an immunoenhanced analogs relative to the level of T-cell activation (i.e., number of epitope-specific CTLs) induced by immunization with the parent peptide. A 50-fold increase in T-cell activity is an especially preferred level of immunoenhancement.

As used herein, an "immunogenic analog" refers to a peptide with one or more residues of the wild-type amino acid sequence substituted with an alternative amino acid sequence identified by the immunoenhancement filter of the disclosed methodology. Coordinated substitutions are often carried out to regulate or modify (e.g., increase) immunogenicity of a natural peptide.

As used herein, "training phase" refers to a systematic and analytical process to discover relevant patterns of immediate interest within a specific dataset.

As used herein, the terms "empirical scoring matrix (ESM)" or "position specific scoring matrix (PSSM)" refer to an array of numbers indicative of the frequency of occurrence of various amino acids residues at each position in a set of peptides of prescribed fixed-length.

The terms "prediction" and "predicting" are used herein refer to the use of the present teachings to estimate properties (e.g., ability to bind to MHC class I allele, likelihood of being efficiently processed and presented by APC, uniqueness to target antigen, immunogenicity) of amino acid sequences representing putative T-cell epitopes.

As used herein, an "epitope" refers to a peptide comprising an amino acid sequence that is capable of stimulating an immune response. The MHC class I epitopes identified by the methodology and processes disclosed herein can be used in compositions (e.g., vaccines) for stimulating an immune response directed to the target antigen. In preferred embodiments, epitopes according to this definition represent peptides which are likely to be non-covalently bound to the binding cleft of a class I MHC molecule on the surface of antigen presenting cells in a manner which facilitates it interaction with T-cell receptors (TCR).

As used herein, the terms "MHC class I binder" and "MHC peptide" are used to refer to peptides having a high known or predicted binding affinity for a mammalian class I major histocompatibility complex (MHC) molecule.

A "target antigen" as used herein refers to an antigen of interest to which an immune response can be directed or stimulated, including but not limited to pathogenic (e.g., derived from a pathogenic agent) and tumor antigens.

As used herein, a "pathogenic agent" is a biological entity that causes pathological symptoms when present in a mammalian host. Thus a pathogenic agent can be, without limitation, an infectious agent (e.g., a virus, a prion, a bacterium, a yeast or other fungus, a mycoplasma, or a eukaryotic parasite such as a protozoan parasite, a nematode parasite, or a trematode parasite) or a tumor cell (e.g., a lung cancer or a breast cancer cell).

As used herein, the terms "immunogenic composition" and "immunostimulatory sequence" are used to refer to compositions and peptide sequences, respectively, which are capable of inducing an immune response, a reaction, an effect, and/or an event. In some embodiments, such responses, reactions, effects, and/or events can be induced in vitro or in vivo. For example, the induction, activation, or expansion of cells involved in cell mediated immunity, such as CTLs represents an immune response, effect or an event. Representative immunogenic compositions include an immunoenhanced full-length target antigen or a minigene vaccine.

As used herein, the term "vaccine" is used to refer to those immunogenic compositions that are capable of eliciting prophylactic and/or therapeutic responses that prevent, cure, or ameliorate disease.

As used herein, the term "epitope vaccine" generally refers to a composition of several epitopes derived from one or more target proteins of the same, or different pathogen or tumor cell, specific to one or more alleles of interest. The list of epitopes used may include those optimized for natural processing, immunogenicity, uniqueness (e.g., lack of similarity to other self-antigens), population coverage, and predicted disease relevance. For example, an immunogenic composition comprising more than one putative T-cell epitope derived from at least one target antigen linked together, with or without additional amino acids ("spacers") between the epitopes can be used as an epitope vaccine. Thus, an epitope vaccine can stimulate immune responses directed to single or multiple epitopes of one or more antigens.

BACKGROUND

1. Bioinformatics

The field of bioinformatics is premised on the concept that biological entities comprise patterns which be identified and that the information derived from these patterns can be used to understand aspects of complex biological systems, such as the mammalian immune system. The term "immunoinformatics" has recently been coined to refer to the field of bioinformatic research which is focused on providing a better understanding of the immune system.

An immune response involves a series of decision points, such as how a particular antigen is degraded into peptides by a cell's processing machinery, whether or not a particular peptide generated by the proteasome or ER-resident proteases is presented on the surface of an antigen presenting cell, whether or not a particular peptide/MHC complex is recognized by a T-cell receptor, which effector T-cells are activated, and what type of an immune response, if any, is initiated. The outcome of each of these decisions is partially determined by the informational content (identity of the amino acid residue at each position of the peptide) of a putative immunostimulatory sequence. It is well known that peptides which are capable of binding to the same MHC molecule are related by sequence similarity. This observation has led investigators to develop computational methods based on amino acid sequence motifs and position specific scoring matrices (PSSM) or profiles derived from aligning peptide sequences known to bind to particular MHC molecules.

Generally speaking, immunoinformatics refers to the application of computational tools and data processing systems to the study of immunological macromolecules and processes. The fact that the binding preferences of an MHC molecule are primarily determined by its molecular structure, makes the process of epitope-based vaccine design particularly amenable to the use of bioinformatics tools. Although it is appreciated that every step of the antigen-processing/presentation pathway contributes to the specificity of antigen selection, it is widely accepted that the most significant point at which MHC sequence/structure constrains antigen recognition is the incorporation/binding of a T-cell epitope into a MHC/peptide complex. Accordingly, computational methods have traditionally focused on predicting the MHC binding affinity of candidate peptides sequences derived from target antigens of self or foreign origin.

2. T-Cells/MHC

The initiation and regulation of an immune response involves several processing, presentation, and recognition events, which result from the interaction of numerous stimulatory/inhibitory signals and the coordinated interaction of several different types of cells. In order for an amino acid sequence derived from a protein antigen to elicit a T-cell-mediated immune response, the original protein must be processed (e.g., by proteasome cleavage followed by N-terminal trimming by ER-resident peptidases), the processed peptide must bind to an MHC molecule, and a TCR must exist which binds the resulting MHC/peptide complex with sufficient affinity for T-cell activation to occur. Accordingly, a fundamental component of all computational models suitable for identifying T-cell epitopes is an analytical tool which predicts the ability of a candidate amino acid sequences to bind to MHC molecules. The underlying rationale is grounded in the premise that strong MHC binding is a prerequisite for immunogenic epitopes [A. Sette et al., *J. Immunology*, 1994, 153: 5586-5592].

The human major histocompatibility complex (MHC) consists of many genetic loci, including seven loci that encode two distinct classes (i.e., MHC class I and MHC class II) of highly polymorphic cell surface antigens which are crucial to both cellular and humoral immune responses. The class I and class II molecules bind to and present processed peptide(s) to circulating T-lymphocytes. The MHC genes represent the most polymorphic genes known in any mammalian system. A class I MHC molecule contains only a single binding site which is utilized to bind all of the peptides which the molecule is capable of recognizing. Because each MHC molecule is capable of binding many different peptides, the binding interaction is said to be degenerate.

A single T-cell epitope can have varying affinities for different MHC molecules, binding some well, others adequately, and still others not appreciably. MHC alleles have traditionally been grouped according to serologic reactivity which does not reflect the structure of the peptide-binding groove, which can differ among different alleles of the same type. In order for a T-cell epitope to be highly immunogenic it must not only promote stable enough TCR binding for activation to occur, but the TCR must also have a low enough off-rate that multiple TCR molecules can interact sequentially with the same peptide-MHC complex (A. Kalergis et al., *Nature Immunology*, 2001, 2: 229-234).

One consequence of the polymorphic nature of the human MHC is that each distinct MHC molecule has its own rules for peptide binding and each allele preferentially binds different peptides. However a relatively small number of alleles can usually be chosen to cover a majority of population. For example, just three Class I alleles HLA-A2, Cw7, and Cw4 together cover >85% of North American population (i.e., >85% of those in the continental U.S. have at least one of these three alleles There are known relationships between HLA genotype and disease susceptibility. For example, the presence of Class I alleles B27 is strongly associated with the incidence of ankylosing spondylitis (AS) [Tissue Antigens 1997, 49: 116-23]. In fact, while HLA-B27 occurs in 8-10% of individuals, >90% of patients with AS carry this allele [J. Fernández-Sueiro et al., *Clinical Exper. Rheumat* 2004, 22: 465-468].

The main function of MHC molecules is to facilitate the display of unique epitopes on the surface of cells in a configuration which permits their recognition by immune effector cells. MHC molecules function to impart specificity to the processes of T-cell immune recognition and activation. Generally speaking, MHC class I molecules gather endogenous peptide fragments derived from infecting pathogenic agents, or self molecules which are deregulated by tumorigenesis, and display these peptides at the cell surface. The presenting structure, which interacts with the processed peptides, is encoded by the major histocompatibility complex (MHC). This requirement is called "MHC restriction" and it is the mechanism by which T-cells differentiate "self" from "nonself." If a processed peptide is not displayed by the host's endogenous MHC molecules, the host's T-cells will not recognize or respond to the peptide. In contrast, if a processed and presented peptide (MHC/peptide complex) is recognized by T-cells expressing an antigen specific TCR, an immune response is initiated.

T lymphocytes (e.g. T-cells) are antigen-specific immune cells that function in response to a series of events and signals resulting from the interaction of a mammalian immune system with an immunostimulatory antigen. T-cell recognition is restricted to those peptides which endogenous MHC molecules can present. T-cell recognition is the first step in the activation of a cellular program that may lead to cytolysis of the APC, secretion of lymphokines by the T-cell, or signaling to natural killer cells. Interaction with the TCR is dependent on both the peptide and the MHC molecule. CTLs are a subset of T-cells that generally recognize peptides that are bound to class I MHC gene products.

Class I MHC molecules are heterodimers of non-covalently bound MHC-encoded heavy (or alpha) chain, and a non-MHC-encoded B2-microglobulin light chain. There are four separate regions: 1) the peptide binding region, 2) the immunoglobulin-like region, 3) the transmembrane region and 4) a cytoplasmic region. The peptide-binding region is groove which functions to accommodate a peptide ligand of 8-10 amino acid residues. The groove formed from the alpha 1 and alpha 2 regions which interact to form a "floor" of an 8-stranded, beta-pleated sheet with two opposite "walls" consisting of parallel strands of an alpha-helix.

The factors that determine the affinity of peptide-class I MHC interactions have been characterized using biochemical and structural methods, including sequencing of peptides and natural peptide libraries extracted from MHC proteins. Class I MHC ligands are typically eight to eleven amino acids in length. Most commonly, class I restricted peptides are octa- or nonapeptides, which bind a groove in the class I MHC structure framed by two α helices and a β-pleated sheet. Class I MHC molecules also interact with atoms in the peptide backbone. The orientation of the peptides is determined by conserved side chains of the MHC I protein that interact with the N- and C-terminal residues in the peptide. Generally speaking, a peptide binding motif defines the specific combination of anchor residues associated with a good fit (and presumed high affinity binding) for a given HLA molecule. For example, HLA allele B*0702 has a distinct preference for a proline (P) at position 2 and a aliphatic amino acid at the C-terminus while allele A*0101 prefers serine (S) or threonine (T) at position 2 and an aromatic amino acid at the C-terminus [A. Sette et al., *Immunogenetics*, 1999, 50: 201-212].

The geometry of the MHC class I-peptide binding site is relatively well characterized. MHC class I molecules consist of two polypeptide chains, a larger a chain which is encoded in the MHC locus, and a smaller non-covalently associated chain, β2-microglobulin, which is not polymorphic, and is not encoded in the MHC locus. The complete molecule consists of four domains, three formed from the a chain, and one contributed by β2-microglobulin. The peptide binding cleft occurs on the surface of the molecule and is formed from the folded α-helical segments of α1 and α2 domains. The T-cell receptor interacts with this compound ligand, making contact with both the MHC molecule and the peptide antigen fragment.

Much of the binding energy in a peptide/MHC molecular complex arises from main chain contacts between conserved residues in the MHC molecule and the N- and C-termini of the peptide. Additional main chain contacts are made but vary among MHC alleles. Sequence specificity is conferred by side chain contacts of a subset of residues in the peptide (e.g., anchor residues) with pockets that, again, vary among MHC alleles.

The binding of peptidic ligands to the MHC binding groove is specific and is stabilized at both ends by contacts between atoms in the free amino and carboxyl termini of the peptide and invariant sites that are found at each end of the cleft of all MHC class I molecules. Because the amino acid side chains at these positions insert into pockets in the MHC molecule and function to anchor the peptide to the MHC molecule they are commonly referred to as anchor residues. The bound peptide lies in an extended conformation along the groove. Anchor residues can be divided into primary and secondary. Primary anchor positions exhibit strong preferences for relatively well-defined sets of amino acid residues. Secondary positions show weaker and/or less well-defined preferences that can often be better described in terms of less favored, rather than more favored, residues.

Additionally, residues in some secondary anchor positions are not always positioned to contact the pocket on the MHC molecule at all. Thus, a subset of peptides exists that bind to a particular MHC molecule and have a side chain-pocket contact at the position in question and another subset exists that show binding to the same MHC molecule that does not depend on the conformation the peptide assumes in the peptide-binding groove of the MHC molecule. The C-terminal residue is preferably a primary anchor residue. For many of the better characterized HLA molecules (e.g. A2, A68, B27, B7, B35, and B53) the second position (P2) is also an anchor residue. However, central anchor residues have also been observed including P3 and P5 in HLA-B8.

The anchor residues confer sequence selectivity and binding specificity to the interaction. The main anchor residues of human HLA class I molecules occur at positions 2 and the C-terminus of the peptides. Polymorphisms among class I MHO gene products create variation in the amino acids of the alpha 1 and alpha 2 sequences of the peptide-binding groove. Generally speaking, peptide-binding to a particular MHC molecule requires the peptide to have one or more specific amino acids at a fixed position, frequently the terminal or penultimate amino acid of the peptide. Since more stable binding will generally improve immunogenicity, anchor residues are preferably conserved or optimized in the design of analogs, regardless of their position.

3. Immunoinoformatics

Prior Art

Effective prophylactic or therapeutic vaccination requires the administration of an immunogenic composition, or vaccine, comprising one or more epitopes against which an immune response can be mounted. Therefore, the first step in an immunoinformatics approach to T-cell epitope identification is to discern patterns that are potentially immunostimulatory from patterns that are not. Rotzschke and Falk are credited with being the first investigators to describe the pattern of amino acids contained in peptides that were known to bind to MHC molecules (A. De Groot et al., *Vaccine* 2001, 19: 4385-4395). They called these patterns "MHC Binding Motifs," and suggested that motifs which were present in amino acid sequences of peptides which were known to bind to particular MHC molecule, could be used to identify T-cell epitopes that are likely to be capable of binding to MHC, engaging T-cell receptors and activating effector T-cells (Falk, K. et al., *Nature* 1991, 351:290-296 and Rotzschke O. et al., *Eur J Immunol* 1991, 21: 2891-2894).

The discovery of MHC binding motifs prompted the development of bioinformatics pattern matching tools suitable for use in the process of epitope-based vaccine design. The first MHC-binding-motif based algorithms were described in the early 1990s [Rammensee, H. et al., *Immunogenetics*, 1995, 41: 178-228]. An MHC binding motif requires the occurrence of stipulated residues at specific positions in a peptide sequence. Generally speaking, binding motifs characterize the peptide specificity of different MHC alleles in terms of dominant anchor positions with a strong preference for a restricted set of amino acids. For example, the best-studied human class I allele, HLA-A*0201, has anchor residues at peptide positions P2 (accepting leucine and methionine) and P9 (accepting valine and leucine).

It has become apparent that sequence-based motifs do not adequately represent the true repertoire of naturally occurring peptides that can bind well to the relevant HLA molecule [Buchsbaum, S., et al., *Immunogenetics* 2003, 55: 172-176] and it is appreciated that the ability of a peptide to bind to a MHC molecule cannot be explained solely by the presence or absence of a few anchor residues. Generally speaking, algorithms based on binding motifs have low prediction accuracy, because only 60 to 70% of binders may contain the motif. In addition, if a peptide motif is used to identify candidate peptides which satisfy the motif requirements, then candidate epitopes cannot be prioritized or ranked among themselves. Therefore, although motifs are simple to understand and have been widely exploited, their utility is limited by the fact that they only make binary decisions. A candidate peptide either is, or is not, predicted to be a binder. Accordingly, an investigator who uses a motif-based selection method is left with a large number of candidate epitopes which have to be tested empirically.

The philosophy underlying the prior art algorithms, as well as the algorithm disclosed herein, is essentially that the higher the binding affinity of a peptide to the MHC, the higher the likelihood is that the peptide represents a T-cell epitope. In general, matrix-based methods assume that the strength of binding of an epitope to the MHC allele is given by the sum of independent binding contributions of each of the peptide's amino acids. Accordingly the methodology basically assumes that the peptide's binding energy is the sum of the binding energies of each amino acid at its respective position. The binding strength is typically determined empirically as an IC50 value (i.e., the concentration of the peptide inhibiting the binding of a reference peptide in half of the binding sites) or as the half-life of binding for the MHC/peptide complex.

A matrix is essentially a refined motif which considers all of the residues at every position of a MHC binding peptide. Profile matrix-based methods for the prediction of T-cell epitopes of varying HLA restriction are also known, including SYFPEITHI (University of Tubingen; http://www.syfpeithi.de) [Rammensee et al., *Immunogenetics* 1999, 48: 89-97] and BIMAS ("Bioinformatics and Molecular Analysis Section" of the National Institutes of Health, http://bimas.dcrt.nih.gov/molbio/hla_bind) [K. Parker et al., *J. Immunology,* 1994, 152: 163-175].

SYFPEITHI provides scores which are based on the presence of certain amino acids in particular positions along the MHC-binding groove. It uses motif matrices deduced from refined motifs based on the pool sequence and single peptide analysis of natural ligands. Putative binding sequences for various human MHC class I molecules are ranked according to the presence of primary and secondary anchor amino acids and favored and disfavored amino acids.

BIMAS identifies and ranks potential T-cell epitopes based on predicted binding affinity scores (i.e., in the case of the HLA-A2 matrix theoretical half-time dissociations MHC/peptide complexes) for the HLA molecule(s) of interest. However, no further trimming of the list of peptides is generally done, leaving the scientist to depend solely on the predicted binding data to select epitope candidates for further study.

4. Epitope Identification Algorithm

Overview

The epitope identification algorithm (EIA) disclosed herein provides a new matrix-based method for predicting the binding affinity of a peptide derived from pathogenic or tumor associated target antigen(s) to a particular MHC class I molecule. The disclosed methodology provides additional advantages over the prior art algorithms because it provides additional analytical tools (e.g., filters) which allow investigators to design vaccines which comprise synthetic immunogenic analogs characterized by more efficient processing, enhanced presentation (relative to the native epitope) to T-cells, and/or a reduced risk of eliciting an off-target immune response that can trigger autoimmunity.

The disclosed methodology and epitope identification algorithm (EIA) have a number of distinguishing characteristics which confers the disclosed selection/optimization processes with an improved ability to predict T-cell epitopes compared to existing computational tool. As disclosed herein the EIA of the invention describes 3 (three) additional steps (filters) that can be used in various combinations, to trim a set of potential T-cell epitope candidates. More specifically, the invention provides a self-similarity filter, an immunoenhancement filter and a natural processing filter.

The binding affinity filter disclose herein is essentially a profile matrix (S. Altschul et al., *Nucleic Acids Res* 1997, 25: 3389-3402) which is trained to predict strong binders according to a unique methodology which differs in several key aspects from how prior art matrices are trained. The differences are explained in detail in the section describing the binding affinity filter. Briefly, we use data clustering and Bayes statistics to better capture the information that is present in the training data, resulting in a superior binding affinity prediction model.

The binding filter disclosed herein can be used as the basis of a computer assisted method for predicting (e.g., identifying) T-cell epitopes that are likely to bind to an MHC class I allele of interest. The invention also provides a natural processing filter which can be used to identify and reject candidate T-cell epitopes which are unlikely to be presented to T-cells due to impaired cellular processing. The invention further provides a self-similarity filter which can optionally be used in the disclosed computer assisted methodology. In practice, the self-similarity filter of the invention allows an investigator to eliminate candidate epitopes which are not unique to the target antigen. In an additional aspect, the invention also provides a methodology for the identification of anchor-modified immunogenic analogs which elicit an enhanced immune response relative to the native epitope of a MHC class I restricted T-cell epitope.

The disclosed scoring matrix encodes all aspects of an allele's binding preferences and is not limited to the informational content of the primary/secondary anchor residues of known epitopes. As shown herein, the predictions based on the disclosed methodology correlate well with published data reporting the results of empirical studies. Accordingly, the disclosed algorithm offers significant advantages relative to the use of allele-specific binding motifs, and has the potential to significantly conserve human and financial resources.

The candidate T-cell epitopes identified, or optimized, with the methodology disclosed herein can be used to design effective vaccines for infectious diseases, cancer, and autoimmune diseases, as well as for the development of in vitro methods for evaluating cellular immunity. Accordingly, the epitopes find utility, individually or in combination, as the basis of a gene-, vector-, peptide-, protein- or cell-based prophylactic or therapeutic vaccine intended to elicit an antigen-specific T-cell immune response. In one embodiment, the disclosed data processing system can be used to design a recombinant full-length protein antigen which is engineered to incorporate one or more amino acid substitutions which the immunoenhancement and binding filters disclosed herein indicate are likely to enhance the immunogenicity of the target antigen. In an alternative embodiment, the disclosed methodology can be used to design a synthetic multi-epitope vaccine containing one or more epitope, or one or more immunogenic analogs, derived from at least one target antigen.

5. Filters

Binding Filters

As explained more fully herein, the disclosed methodology provides a Bayes-corrected scoring matrix-based method which can be utilized in a process which identifies and ranks candidate epitopes derived from a protein of interest on the basis of its predicted binding affinity for an HLA class I allele. Using the methodology disclosed herein, candidate T-cell epitopes can be identified based on four criteria: 1) predicted binding affinity to the HLA allele of interest, 2) specificity for the target antigen, 3) likelihood that the sequence will be naturally processed by the proteasome, and 4) amenability to immunoenhancing modification. The disclosed methodology allows investigators to rationally design therapeutic and prophylactic T-cell vaccines which will elicit a protective immune response with minimal risk of off-target autoimmune activity.

In one embodiment the invention provides a data processing system which utilizes a binding affinity prediction algorithm in the context of a computer-based method for the automated prioritization of candidate T-cell epitopes present in an immunologically relevant protein of interest. The binding affinity prediction algorithm (BSM) training phase involves three steps: 1) Collecting and curating the input data, 2) Calculating an empirical scoring matrix (ESM), and 3) Calculating a Bayes-corrected scoring matrix (BSM).

The input for the training phase is a set of strong binders pooled from several public databases. While similar in concept to positional profile scoring matrix (PSSM), there is a significant difference in how the disclosed ESM is computed from the sequence information of the training peptides. This difference, we believe, contributes to the improved performance of our algorithm. The final product of the training phase is a Bayes-corrected scoring matrix (BSM). Without wanting to be bound to any particular theory, it is believed that the differences in how the informational content of the training peptides is used to derive the ESM confers the disclosed methodology with improved accuracy for predicting T-cell epitopes relative to the performance of prior art algorithms. It is further believed that the improved accuracy contributes to the improved performance of the disclosed methodology over prior art T-cell identification algorithms.

Accordingly, the disclosed algorithm provides a bioinformatics tool, in the context of a Bayes-corrected scoring matrix, also referred to herein as a binding filter, which can be used to predict the relative binding affinities of candidate peptides based on the informational content of the sequence information contained in the training set. An epitope selection matrix summarizes the binding specificities of a single HLA allele of interest. The disclosed epitope selection process can be used to predict HLA class I restricted T-cells for any class I allele selected from the group consisting of HLA-A, HLA-B, or HLA-C for which there is sufficient data to prepare a training set of peptides. A skilled artisan will readily appreciate that allele selection can be driven by the goal of maximizing coverage in a given population, or based on a known association between a particular HLA allele and susceptibility to a particular disease (such as presence of HLA-B27 in ankylosing spondylitis, or course of disease progression.

1) Training Phase

FIG. 1 provides a diagram of the steps involved in modeling the binding preferences of a particular MHC allele based on the informational content of a set of training peptides comprising allele-specific peptides which are known to be strong binders to the allele that is being modeled. The informational content and patterns contained in the amino acid sequences of the peptides selected for inclusion in the training set are used to define an epitope selection matrix (ESM). The resulting ESM is subsequently utilized to identify and rank candidate peptides, derived from an immunologically relevant antigen, for their ability to bind to particular HLA class I molecules. Input data, which provides information relating to the binding affinity of peptides known to bind to a particular HLA allele of interest, can be obtained from a publicly accessible epitope database, such as, but not limited to:

JenPep (http://www.jenner.ac.uk/Jenpep2/),

MHCBN (http://www.imtech.res.in/raghava/mhcbn/), and

FIMM (http://sdmc.lit.org.sg:8080/fimm/).

In some embodiments, the data which is utilized to select peptides for inclusion in the training set represents a combination of amino acid sequence information and quantitative binding affinity data; in other instances the data is a combination of sequence information and qualitative binding data based on findings reported in the literature. A skilled artisan will readily acknowledge that HLA binders reported in publicly accessible databases are routinely classified as strong, intermediate, or weak binders. These classifications are made by the database curators based on author statements. Note that quantitative binding information such as IC50 is missing for most peptides in these databases. Moreover, it would be unreasonable to select strong binders based on a fixed IC50 threshold, since the IC50 values are measured with respect to a test peptide, and test peptides vary from paper to paper. Therefore, database curators generally rely on author statements to classify peptides as strong, intermediate, weak binders, or non-binders. This qualitative annotation makes it possible to download, for example, only strong binders to an HLA allele of interest. For example, it is possible to obtain strong binders to allele HLA-A2.

Based on publicly available information, a training set is identified which includes unique, naturally occurring peptides 9 or 10 amino acids in length (9-mers and 10-mers, respectively) which are known to bind to a particular MHC class I allele. The selected sequences are reviewed to ensure that they represent naturally occurring peptides (e.g., selected sequences are compared to wild type protein to verify that the sequence occurs in the wild type protein from which the peptide was obtained). Peptides comprising amino acid sequences which do not occur in the wild-type version of its source protein are not included in the training set. As a result of this curation process, only verified "naturally occurring" sequences are retained in the training set. For example, potential training set peptides can be verified and curated for inclusion in a training set for a particular allele of interest by searching for identical peptides in SwissProt protein database using the pattern search tool PattInProt, available online at: http://npsa-pbil.ibcp.fr/cgi-bin/npsa_automat.pl?page=/ NPSA/npsa_pattinprot.html. Suitable parameters for this search are as follows: Protein_Database='SwissProt'; Similarity_Level=100%. If an exact match does not exist in SwissProt, then the peptide is removed from the training set. The resulting training set represents a collection of verified (e.g., curated) naturally occurring peptide sequences (e.g., epitopes) which are known to be strong binders to the MHC molecule of interest. For the binding filter to provide a minimum acceptable level of accuracy, the training set should contain at least (e.g. 40 or more) unique peptides. It is to be understood that training sets containing fewer peptides can also be used. However, based on the data provided herein, the validity of the predictions derived from a training set containing less than about 40 (e.g. less than 37, 38, 39, 40 or more) peptides should not be assumed to be reliable.

2) Calculation of Empirical Scoring Matrix

An empirical scoring matrix (ESM), defined below, summarizes frequency of occurrence of each of the 20 amino acids at each position in the set of training peptides. The ESM resulting from the methodology disclosed and claimed herein is a 20 by 9 matrix. While similar in concept to a positional profile scoring matrix (PSSM), there is a significant difference in how the ESM of the invention is computed from the training set [Gribskov et al., PNAS 1987, 84: 4355-8. A positional profile scoring matrix, P is a matrix whose $(i,j)^{th}$ entry contains the frequency of occurrence of amino acid i in position j in the training set. In other words:

$$P(i, j) = \frac{\text{\# peptides containing } i \text{ at position } j}{\text{total \# peptides}} \qquad (1)$$

If the training set contains peptides that are highly similar in sequence to each other (as happen quite frequently with strong binders to an HLA molecule), the identical amino acids contribute multiple times to the PSSM. This has the effect of giving disproportionably large weight to repeated amino acids at positions that are potentially irrelevant to binding to the HLA molecule.

In order to avoid the limitations inherent in a PSSM, we begin by combining similar peptides into clusters based on sequence similarity. Typically, 65% sequence identity is used as a threshold for defining the clusters. In practice, a suitable threshold of sequence identity can range from about 60% to about 95% sequence identity. Accordingly, suitable threshold values include, but are not limited to, 60%, 65%, 70%, 75%, 80%, 85%, 90%, and 95%. Then, for each amino acid and at each position, we compute the fraction of clusters that contain the amino acid at that position. The result is the empirical scoring matrix, F.

Mathematically, the $(i,j)^{th}$ entry F is given by $$F(i, j) = \frac{n(i, j)}{N_j}, \qquad (2)$$

where $n(i,j)$ is the number of clusters containing amino acid i at position j, and $N_j = \Sigma_i n(i,j)$. It should be noted that equation (2) reduces to a value of one (1) when the peptides are clustered at 100% sequence identity. Step 2 of Example 1 (Derivation of a Bayes-Corrected Scoring Matrix from Binding Data for Murine Class I Allele H-2K$^d$) of the instant disclosure illustrates how a set of training peptides are clustered for use in computing an ESM.

Because a training set may contain both 9-mer and 10-mer peptides, special care must be taken to properly combine the informational content of all of the peptides into a single 20 by 9 ESM. In practice, the columns of the matrix represent the following positions of the training peptides: a) columns 1-4 of the ESM will correspond to positions 1-4 of the 9-mers and 10-mers; b) column 5 of the ESM corresponds to position 5 of the 9-mers and positions 5 and 6 or the 10-mers; and columns 6-9 of the ESM will correspond to positions 6-9 of the 9-mers and 7-10 of the 10-mers The values of the ESM at the flanking positions (positions 1-4 and 6-9 for 9mers, 1-4,7-10 for 10mers), are computed by equation (2). This gives the values F(i,j) when i is between 1-4 and 6-9.

To compute F(i,5), the central positions (position 5 for 9-mers; 5 and 6 for 10-mers) are combined:

$$F(i, 5) = \frac{1}{2}\left(\frac{\text{\# 9mer clusters containing } i \text{ at position 5}}{\text{total \# clusters of 9mers}} + \frac{\text{\# 10mer clusters containing } i \text{ at position 5 or 6}}{\text{total \# clusters of 10mers}}\right)$$

3) Calculation of Bayes-corrected Scoring Matrix

The relative frequency of an amino acid at each position, even adjusted as in our method, may not be an optimal indicator of the degree to which its presence at the corresponding position is required for strong HLA binding. In fact, a residue that occurs frequently at a particular position in the training set may simply be an amino acid that occurs frequently in general. Accordingly, it is quite common in the art to adjust normalized amino acid scores by frequency of occurrence in a protein database such as SwissProt.

The adjusted scoring matrix F' is obtained from the scoring matrix F by normalizing F by the SwissProt frequencies:

$$F'(i, j) = \frac{F(i, j)}{S_i}, \quad (3)$$

where $S_i$ is the frequency of amino acid i in SwissProt as listed at http://www.expasy.org/sprot/relnotes/relstat.html.

A separate issue with empirical scores is the problem of "overfitting." An example of overfitting is as follows: if an amino acid never occurs at a given position in the training set (as is quite common with small data sets), then a real T-cell epitope that happens to have this amino acid at the corresponding position will receive a low score, and will be erroneously rejected by the model. In general, overfitting implies lower accuracy of the resulting model. To address this issue, empirical scores are often adjusted in the art using pseudo-counts as described in [S. Altschul et al., *Nucleic Acids Res.* 1997, 25: 3389-3402]

In order to minimize the likelihood that the disclosed ESM will overfit the training set data, Bayes statistics [D. Heckerman, *A tutorial on learning Bayesian networks*, Microsoft Research Tech Rep 1995, MSR-TR-95-06, pp. 2-5] is used to simultaneously address the problems of overfitting and unequal distribution of amino acids in a principled way.

Specifically, for each amino acid i and position j, we compute:

$$C(i, j) = \frac{\frac{F(i, j)}{S_i} + \frac{e}{N_j}}{1 + \frac{e}{N_j}}. \quad (4)$$

Here, F(i,j), $S_i$ and $N_j$ are as before, and e is a single parameter that controls the trade-off between observed (empirical) and expected (SwissProt) frequencies at each position. The case e=0 corresponds to (3). We use e=10 in our calculations.

Taking the natural log in (4), we obtain Bayes-corrected Scoring Matrix B, or BSM.

$$B(i, j) = \log\left(\frac{\frac{F(i, j)}{S_i} + \frac{e}{N_j}}{1 + \frac{e}{N_j}}\right). \quad (5)$$

iv). Binding Prediction

4) Binding Prediction

After computing the BSM, the resulting epitope scoring matrix is used to identify and rank candidate T-cell epitopes based on the predicted likelihood that amino acid sequence will bind to the particular HLA allele that is being modeled. The outcome of the binding prediction step of the disclosed methodology is a rank-ordered list of peptides which are predicted to be strong binders to an HLA allele of interest.

Figure 2:
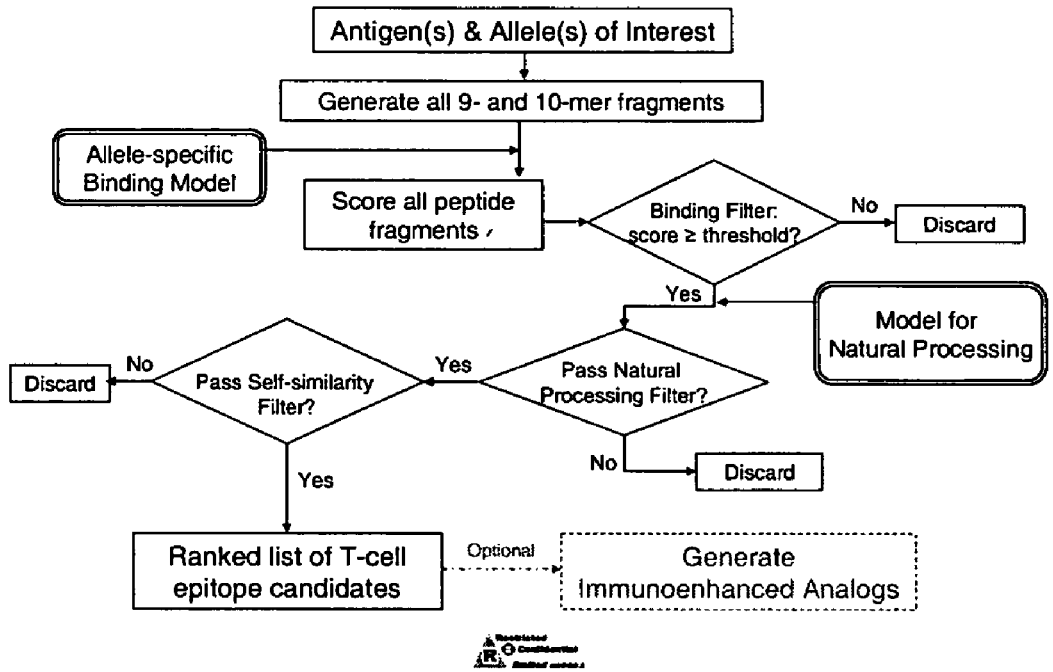

The binding prediction method is diagramed is FIG. 2. All possible 9-mer and 10-mer peptides (longer and shorter frames are not considered because most Class I HLA binding peptides are 9 to 10 amino acids in length) are derived from a target protein (i.e. antigen), and using the values from the BSM a predicted binding score is computed for each of the candidate T-cell epitope peptides. FIGS. 3*a* and 3*b* illustrate how a binding score is calculated for a 9-mer and 10-mer candidate T-cell epitope, respectively. Briefly, the score is calculated as follows: for each 9-mer $a_1 \ldots a_9$, its score is obtained by simply adding the appropriate entries of the BSM:

$$S(a_1 \cdots a_9) = \sum_{i=1\ldots 9} B(a_i, i)$$

FIG. 3(*a*) details how a 9-mer peptide AYCRWGLNL (SEQ ID NO:103) is assigned a score based on the BSM shown in Table 4.

Score [A Y C R W G L N L (SEQ ID NO:103)]=B(A,1)+B(Y,2)+B(C,3)+B(R,4)+B(W,5)+B(G,6)+B(L,7)+B(N,8)+B(L,9)=0.17+2.50−1.10−0.03−1.10−0.21−0.38++0.65+1.65=2.15

For each 10-mer $a_1 \ldots a_{10}$, its score is obtained by adding the scores of the 8 flanking amino acids and the average of the scores of the middle two positions:

$$S(a_1 \cdots a_{10}) = \sum_{i=1\ldots 4} B(a_i, i) + \sum_{i=7\ldots 10} B(a_i, i-1) + \frac{B(a_5, 5) + B(a_6, 5)}{2}$$

FIG. 3(b) illustrates how the 10-mer peptide AYCRWTGLNL (SEQ ID NO:104) is assigned a score based on the same BSM from Table 4.

Score [A Y C R W T G L N L (SEQ ID NO:104)]=B(A,1)+ B(Y,2)+B(C,3)+B(R,4)+{B(W,5)+B(T,5)}/2+B(G,6)+B(L, 7)+B(N,8)+B(L,9)=0.17+2.50−1.10−0.03+{−1.10−0.06}/ 2−0.21−0.38+0.65+1.65=2.67

In practice, application of the above-described binding filter generates a list of 9-mer and 10-mer epitope candidates, ranked by their BSM scores. The percentile corresponding to a given score is the fraction of randomly generated peptides having scores below it. Generally speaking, peptides characterized by scores in the 95$^{th}$ percentile or higher are considered to be strong binders. Note that ordering peptides by their binding score or by their percentile produces identical ranked lists of epitope candidates.

Natural Processing Filter

Prior to binding class I MHC molecules, a protein antigen is "processed", meaning that it is subjected to limited proteolytic cleavage in order to produce peptide fragments. The proteasome performs antigen processing for the class I pathway. HLA Class I-restricted T-cell epitopes are generated by proteasomal cleavage of a full protein, followed by N-terminus trimming of the resulting fragments by ER-resident aminopeptidases (H. Snyder et al., J. Exp. Med. 1994, 180: 2389-2394). Peptides that are not efficiently cleaved out by the proteasome, or improperly trimmed, fail to be exported to cell surface. Since presentation on the cell surface of an antigen presenting cell is a prerequisite for recognition by T-cells, peptides which are likely to be poorly presented represent suboptimal candidates for inclusion in an epitope-based vaccine. Since epitope vaccines are typically designed to contain one or more epitopes with high MHC binding affinities and defined immunogenicity, the efficiency of epitope processing can be a dominant variable affecting the efficacy of the vaccine. Therefore, the efficiency of epitope processing and presentation is a critical aspect of designing multi-epitope vaccines.

Accordingly, another aspect of the invention provides a natural processing filter which can be used in combination with the above-described binding affinity filter to identify and screen out peptides that are unlikely to be presented to T-cells due to impaired cellular processing. It is well known that the particular amino acids flanking individual CTL epitopes may alter the susceptibility of the antigen to proteolytic cleavage. The filter disclosed herein was defined by searching candidate epitopes' flanking residues for the presence of one of several amino acid motifs which appear to be indicative of a decreased likelihood of presentation on the cell surface. Because presentation on the cell surface in the context of an HLA molecule is a prerequisite for recognition by T-cells, peptides possessing one or more of these interfering motifs are suboptimal candidates for inclusion in an epitope-based vaccine.

In order to identify peptide sequences which have a low likelihood of being a naturally processed peptide, a statistical technique is used to define indicator motifs which when present at a peptide's N-terminus, are associated with a decreased likelihood of being processed. This information was used to design a "natural processing filter" which can be used to screen potential T-cell epitopes for the presence of one or more of these indicator motifs.

The steps for training the natural processing filter are illustrated in FIG. 1c. Briefly, 1) naturally processed, Class I-restricted T-cell epitopes, regardless of origin (viral, bacterial, mammalian, etc.), length, and Class I allele specificity, were extracted from the aforementioned epitope databases; 2) the frequency of occurrence of each amino acid at the N-terminus (pos. P1') and at three consecutive positions to the left of the N-terminus (P3-P1) was obtained; 3) for each amino acid at each position, a statistical test based on the frequency of occurrence of this amino acid in SwissProt was performed; and 4) p-values resulting from the significance tests were corrected for multiple tests by multiplying by 160 (2 tests per amino acids per position).

For example, the frequency of proline in SwissProt is 0.049. Therefore, among the 704 peptides, one would expect on average, 704×0.049=33 prolines at any given position. The actual number of prolines at P1 in this dataset is substantially fewer: 7 (seven). The probability of observing 7 or fewer prolines among 709 possible amino acids is given by the partial sum of the binomial distribution with mean 0.049 and N=709, or 2.2×10$^{-8}$. This is a one-sided p-value from the binomial test. The low p-value indicates that the presence of a proline at P1 of a peptide is associated a decreased likelihood of natural processing.

Based on this procedure, we have identified three (3) amino acid/position combination with Bonferroni-corrected p-values statistically significant at the 0.01 level. All three were associated with a decreased likelihood of natural processing. The combinations are: (1) Proline at the N-terminus (p<10$^{-10}$); (2) a Leucine at the N-terminus (p<10$^{-4}$), and (3) a Proline at the position immediately preceding the N-terminus ((p<10$^{-5}$). Accordingly, the disclosed computer assisted methodology can be optionally modified to implement a natural processing filter based on the following rule: reject an epitope candidate if it has a proline at P1 or P1', or a leucine at P1'.

Self-Similarity Filter

The Bayes-corrected scoring matrix generates a list of peptides identified as potential T-cell epitopes. Some of the peptides identified by the binding filter may be identical, or highly similar, to fragments of other human proteins. In other words some of the peptides are not unique to the target protein. We refer to peptides that are identical, or highly similar, to fragments of other non-target proteins, as "self-similar peptides". For example, if the protein of interest is a tumor-associated antigen, some of its fragments may occur in other self proteins.

With regard to peptide sequences, the term "sequence identity" likewise means that two peptide sequences are identical (on an amino acid-by-amino acid basis) over a window of comparison. The percentage of amino acid sequence identity (or percentage of amino acid sequence similarity) is similarly calculated by comparing two optimally aligned amino acid sequences over the window of comparison, determining the number of positions at which the identical amino acid residues occur in both amino acid sequences to yield the number of matched positions, dividing the number of matched positions by the total number of positions in the window of comparison, and multiplying the result by 100 to yield the percentage of sequence identity (or percentage of sequence similarity). The terms "percent identity," "percent identical," "percentage of sequence identity, and "percent sequence identity" are used interchangeably.

Alignment and comparison of relatively short sequences (less than about 30 residues) is typically straightforward, and identity between relatively short amino acid sequences can be easily determined by visual inspection. Comparison of longer sequences can require more sophisticated methods to achieve optimal alignment of two sequences. Analysis with an appropriate algorithm, typically facilitated through computer software, commonly is used to determine identity between longer sequences. When using a sequence comparison algorithm, test and reference sequences typically are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. A number of mathematical algorithms for rapidly obtaining the optimal alignment and calculating identity between two or more sequences are known and incorporated into a number of available software programs. Examples of such programs include the MATCH-BOX; MULTAIN, GCG, FASTA, and ROBUST programs for amino acid sequence analysis, and the SIM, GAP, NAP, LAP2, GAP2, and PIPMAKER programs for nucleotide sequences. Suitable software analysis programs for amino acid and sequence analysis include the ALIGN, CLUSTALW (and BLAST programs (e.g., BLAST 2.1, BL2SEQ, and later versions thereof).

The inclusion of self-similar peptides in their native form in a vaccine composition runs the risk of eliciting an off-target autoimmune response. For example, published reports documenting the T-cell mediated destruction of melanocytes or pancreatic islet β-cells following immunotherapy provide examples of the unwanted consequences of using a peptide which because of its self-similarity to a non-target antigen can induce an unwanted autoimmune response to a non-target protein. [Van Elsas, et al., *J. Exp Med* 1999, 190: 355; Ludewig, et al., *J. Exp. Med.* 2000, 191: 795-804] The use of the disclosed self-similarity filter allows an investigator to address safety concerns associated with the risk of using peptides which are not unique to the target antigen as a component of a gene-, protein-, vector-, or cell-based cancer vaccine.

It is also appreciated that peptide sequences (e.g., epitopes) which occur in multiple self-proteins are more likely to have induced the deletion or inactivation of specific T-cells and, as such, may not be effective at eliciting a cellular immune response. The consequences of T-cell education and clonal deletion provides a second rationale for identifying and eliminating conserved self-similar epitopes from proposed immunogenic compositions.

As shown herein, the self-similarity filter of the invention can be used to identify and eliminate self-similar epitopes from the list of candidate epitopes resulting from the application of the binding filter. In practice, each 9-mer and 10-mer peptide in the list of candidate epitopes ("query peptide") is matched against the entire human genome. A fragment is considered self-similar if another human protein contains a fragment that is either identical to, or differs by at most 2 amino acids from the query peptide and, in the latter case, and the mismatches are restricted to the MHC anchor residues (i.e., residues 2 and 9 or 10)

A number of publicly available tools can identify if a given peptide is self-similar, by query this peptides against a protein database. Examples include, but are not limited to, (a) PATTINPROT (http://npsa-pbil.ibcp.fr/cgi-bin/npsa_automat.pl?page=npsa_pattinprot.html), a software tool that finds matches within the Swiss-Prot protein database, and (b) BLASTp (http://www.ncbi.nlm.nih.gov/BLAST/producttable.shtml#begin), that can search a number of databases in addition to Swiss-Prot such as "nr" and "refseq."

Immunogenicity Enhancement Filter

As used herein, the twenty conventional amino acids and their abbreviations follow conventional usage. It is to be understood that as used herein the term "amino acid," includes the 20 naturally occurring amino acids, as well as those amino acids which are modified post-translationally in vivo, including for example hydroxyproline, phosphoserine and phosphothreonine, and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The twenty (20) naturally occurring amino acids are commonly divided into six classes based on common side chain properties: 1) hydrophobic: norleucine (Nor), Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe. Conservative amino acid substitutions may involve exchange of a member of one of these classes with another member of the same class. Non-conservative substitutions may involve the exchange of a member of one of these classes for a member from another class. In making such changes, according to certain embodiments, the hydropathic index of amino acids may be considered. The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within .+−0.2 is included. In certain embodiments, those that are within +−0.1 are included, and in certain embodiments, those within .+−.0.5 are included.

Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5);

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein. A skilled artisan will be able to determine suitable variants of candidate T-cell epitopes using well-known guidelines and techniques.

It is well known in the art that HLA Class I binders modified at anchor positions (position 2 and the C-terminus position of the peptide), are often more immunogenic than the wild-type peptide due to improved binding to the HLA molecule (G. Lipford et al., *Immunology* 1995, 84: 298-303). At the same time, T-cells specific for the modified peptide generally also recognize the wild-type peptide, since the mutations are restricted to residues that do not make contact with the T-cell receptor. Based on this knowledge, we introduce as part of this invention, an immunogenicity enhancement filter, to identify anchor-modified analogs that comprise substitutions/mutations that optimize peptide/MHC binding interactions at the anchor positions.

In practice, the immunoenhancement filter of the invention is used to evaluate the effect of substituting each of the twenty naturally occurring amino acids at anchor residues (typically, position 2 and the C-terminus position of HLA Class I allele anchor positions) of a candidate T-cell epitope which has been predicted to bind to an HLA class I allele of interest and which has passed the self-similarity of the invention. In practice, the effects of introducing an amino acid substitution at each of the anchor positions are evaluated on the predicted binding affinity of each of the analogs. The proposed substitutions are evaluated sequentially (i.e., one at a time at each position). During the course of the analysis, each anchor residue is evaluated one at a time, with each of the 20 amino acids being substituted at each of two positions. The binding score of the peptide containing the substitution (e.g., putative immunogenic analog) is computed using the above-described binding affinity filter (i.e., Bayes-corrected scoring matrix), and compared to the predicted binding score of the parental peptide. Generally speaking, the peptide with the highest score is selected as the immunogenic analog. If none of the proposed substitutions/replacements result in an analog that is predicted to have a binding score that is higher than the binding score of the parental peptide, then no analogs are suggested.

In practice, the disclosed immunoenhancement filter can be used to identify substitutions within anchor residues of T-cell epitope candidates to improve their immunogenicity. In one embodiment, this aspect of the invention can be used to enhance the immunogenicity of an epitope derived from an antigen which is derived from a self protein, as a tumor-associated antigen. Tumor-associated antigens are frequently characterized by suboptimal MHC affinities because of the effects of central and peripheral tolerance of the TCR repertoires and are generally considered to be poorly immunogenic. Therefore, in order to design an effective cancer vaccine it may be necessary to enhance the immunogenicity of putative class I restricted tumor associated antigens. A skilled artisan will acknowledge that the ability to use an immunoenhanced analog that is capable of eliciting an immune response that is cross-reactive with the target antigen is preferable to using a weakly immunogenic self-epitope.

Computer Hardware and Software

The computer-requiring steps in a method of predicting T-cell epitopes in a target protein can minimally involve: (a) inputting into an input device, e.g., through a keyboard, a diskette, or a tape, data that can be used to compute a Bayes-corrected scoring matrix which utilizes the informational context of a Training Set of peptides which are known to bind to the particular HLA allele that is being modeled; and (b) determining, using a processor, a binding score for each candidate T-cell epitope derived from a target protein based on the values on the scoring matrix.

The invention described herein can be implemented in computer hardware or software, or a combination of both. Generally speaking, various embodiments of the epitope identification algorithm described herein can be achieved using a computer program providing instructions in a computer readable form. For example, the invention can be implemented by one or more computer programs executing on one or more programmable computers, each containing a processor and at least one input device. The computers will preferably also contain a data storage system (including volatile and non-volatile memory and/or storage elements) and at least one output device.

Program code is applied to input data to perform the functions described above and generate output information. The output information is applied to one or more output devices in a known fashion. The computer can be, for example, a personal computer, microcomputer, or work station of conventional design. One of skill in the art will readily recognize that different types of computer language can be used to provide instructions in a computer readable format. For example, a suitable computer program can be written in languages such as Matlab, S+, C/C++, FORTRAN, PERL, HTML, JAVA, UNIX, or LINUX shell command languages such as C shell script, and different dialects of such languages. Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

Different types of computers can be used to run a program implementing the algorithm described herein. For example, computer programs for predicting T-cell epitopes using the disclosed algorithm can be run on a computer having sufficient memory and processing capability. An example of a suitable computer is one having an Intel Pentium®-based processor of 200 MHZ or greater, with 64 MB of main memory. Equivalent and superior computer systems are well known in the art.

Standard operating systems can be employed for different types of computers. Examples of operating systems for an Intel Pentium®-based processor include the Microsoft Windows™ family, such as Windows NT, Windows XP, Windows 2000 and LINUX. Examples of operating systems for a Macintosh computer include OSX, UNIX and LINUX operating systems. Other computers and operating systems are well known in the art. The data presented herein illustrating various aspects of the invention was producing using software written in the Matlab programming language on a 600 MHz, Intel-based computer with 512 Mb ram, running Windows XP operating system.

Depending upon which filters are employed for a particular use of the algorithm described herein, the resulting data can be presented in a variety of formats. The method can involve the additional step of outputting to a monitor, printer, or another output device. In addition, the data can be compared to a computer database of T-cell epitopes stored in a data storage system. For example, data can be presented in a list, a table or a graphic format. In one embodiment, the data can be presented as a list of candidate peptides ranked in order of their predicted binding scores. In an alternative embodiment, data can be presented by underlying, or emphasizing by other means, epitopes within the protein that is shown on the screen or printed out to a printer.

Although, the invention is illustrated herein, using peptides derived from a particular set of target proteins it is to be understood that the invention is not limited to the use of the antigens exemplified herein. More specifically, the invention contemplates the use of the disclosed algorithm to identify MHC class I binding epitopes from antigens of both foreign and self antigens. Suitable target antigens may be obtained from a wide variety of pathogenic agents (such as, but not limited to viruses, parasites, bacteria and fungi) that infect mammalian hosts, or from a cancer or tumor cell. For example, if the epitope identification algorithm of the invention is used to select epitopes for use in an immunogenic composition (e.g., vaccine) intended to elicit a cell-mediated immune response that is specific for an infectious agent, then it is appropriate to utilize peptide sequences (e.g., 9-mers and 10-mers) derived from pathogen-derived proteins.

In one embodiment the epitope, or epitopes, selected for use in a vaccine may represent a naturally occurring peptide which the binding affinity filter has predicted to be likely to bind to a particular HLA allele. The natural processing filter of the invention may optionally be used in combination with the epitope selection matrix, to design peptide sequences comprising epitopes which are likely to be processed by the intended host's cellular proteases.

In an alternative aspect, an epitope selected for use in a vaccine may be an immunogenic analog of a naturally occurring peptide which has been optimized based on the data obtained by using the optimization filter of the invention in combination with the epitope selection matrix of the invention, as described in Example 8. More specifically, the analog selected for use in an immunogenic composition may represent an anchor-modified analog.

In one aspect, the invention provides an epitope identification/optimization method which can be used to identify peptide sequences suitable for use in a vaccine designed to induce a pathogen-specific immune response. For example, in one application, it may be desirable to elicit an immune response against a virus infecting humans and/or non-human animal species. Examples of virus families against which a prophylactic and/or therapeutic immune response would be desirable include the Picornaviridae family, which includes different genera such as Aphtovirus, Cardiovirus, Enterovirus, Hepatovirus, Parechovirus, and Rhinovirus. Examples of Picornaviruses against which an immune response would be desirable are: Foot-and-mouth disease viruses, Encephalomyocarditis viruses, Polioviruses, Coxsackieviruses, Human hepatitis A virus, Human parechoviruses, and Rhinoviruses. The Caliciviridae family includes different genera associated with epidemic gastroenteritis in humans caused by the Norwalk group of viruses, and other syndromes in animals like the hemorrhagic disease in rabbits, which is associated with rabbit hemorrhagic disease virus, or respiratory disease in cats caused by feline calicivirus.

Another family of viruses against which it may be desirable to elicit an immune response is the Astroviridae, which comprises viruses isolated from humans as well as many different animal species. Human astroviruses are associated with gastroenteritis and young children diarrhea. Alternatively, it may be desirable to confer mammalian hosts with immunity to members of the Togaviridae family of viruses which comprises two genera: alphavirus and rubivirus. Alphaviruses are associated with human and veterinary diseases such as arthritis (i.e. Chikungunya virus, Sindbis virus) or encephalitis (i.e. Eastern Equine Encephalitis Virus, Western Equine Encephalitis Virus).

Rubella virus, which is the only member of the *Rubivirus* genus, is responsible for outbreaks of a mild exanthematic disease associated with fever and lymphoadenopathy. Rubella virus infection is also associated with fetus abnormalities when acquired by a mother during in early pregnancy. Flaviviridae is another virus family consisting of three genera: the flaviviruses, the pestiviruses and the hepaciviruses that includes important human as well as animal pathogens. Many of the *flavivirus* genus members are arthropod-borne human pathogens causing a variety of diseases including fever, encephalitis and hemorrhagic fevers. Dengue Fever Viruses, Yellow Fever Virus, Japanese Encephalitis Virus, West Nile Fever Virus, and Tick-borne Encephalitis Virus are pathogens of major global concern or of regional (endemic) concern. The *Pestivirus* genus includes animal pathogens of major economic importance such as Bovine Viral Diarrhea Virus, Classical Swine Fever Virus, and Border Disease Virus. Hepatitis C Virus (HCV) is the only member of the *Hepacivirus* genus, which is responsible for acute and chronic hepatitis. HCV proteins expressed by a recombinant adenovirus can elicit a protective as well as therapeutic immune response, limiting the consequences of a viral infection affecting 170 million people worldwide.

Alternatively, proteins derived from members of the Coronaviridae family can be analyzed for the presence of epitopes which are predicted to bind to a particular MI-IC class I molecule. For example, protection against the severe acute respiratory syndrome coronavirus (SARS-Co Virus) may be obtained by immunizing with a multiepitope vaccine comprising one or more SARS-CoV protein epitopes including without limitation, naturally occurring or optimized peptide sequences obtained from the nucleocapsid (N) protein, polymerase (P) protein, membrane (M) glycoprotein, spike (S) glycoprotein, small envelope (E) protein or any other polypeptide expressed by the virus. Rhabdoviridae family members including rabies virus can be target of recombinant vaccine expressing viral proteins.

Other possible targets include the Filoviridae family, comprising the Ebola-like viruses and the Marburg-like viruses, which are responsible for outbreaks of severe hemorrhagic fever; the Paramyxoviridae family, comprising some of the most prevalent viruses known in humans, like measles, respiratory syncytial viruses, parainfluenza viruses, and viruses of veterinary interest like Newcastle disease and rinderpest viruses; the Orthomyxoviridae family, including Influenza A, B, and C viruses; the Bunyaviridae family mainly transmitted by arthropod to vertebrate hosts, comprising important human pathogens like Rift valley fever, Sin Nombre virus, Hantaan virus, and Puumala viruses; the Arenaviridae family comprising Lymphocytic choriomeningitis, Lassa fever, Argentine Hemorrhagic fever, and Bolivian Hemorrhagic fever viruses; the Bornaviridae family comprising viruses causing central nervous system diseases mainly in horses and sheep; the Reoviridae family including rotaviruses, the most important cause of severe diarrheal illness in infants and young children worldwide, orbiviruses that can affect both humans and other mammals (bluetongue, epizootic hemorrhagic disease viruses); the Retroviridae family, which is a large group of viruses comprising important human pathogens like human immunodeficiency virus 1 and 2 (HIV-1 and HIV-2) and human t-cell leukemia virus type 1 and 2 (HTLV 1 and 2), as well as non-human lentiviruses such as MaediNisna viruses affecting sheep and goats, equine infectious anemia virus affecting horses, bovine immunodeficiency virus affecting cattle, feline immunodeficiency virus affecting cats; the Polyomaviridae family, which includes small DNA oncogenic viruses, prototype viruses are polyoma and SV40, infecting mouse and rhesus monkey respectively, (BK and JC viruses closely related to SV40 were isolated from human patients); the Papillomaviridae family, which consists of a group of DNA viruses infecting higher vertebrates including humans, and generates warts and condylomas. Papilloma viral infection is associated with the development of cancer in both humans and animals. Human papilloma viruses are associated with cervical cancer, vaginal cancer and skin cancer. The herpesviridae family includes subfamilies in which are classified a number of important pathogens for humans and other mammals. Suitable sources of antigens can be, but are not limited to, herpes simplex viruses 1 and 2, varicella-zoster virus, Epstein-Barr virus, Cytomegalovirus, human herpesviruses 6A, 6B and 7, and Kaposi's sarcoma-associated herpesvirus. Further suitable sources of antigens are members of the Poxyiridae family like Monkeypox virus, Molluscum contagiusum virus, smallpox virus, Hepatitis B virus, the prototype member of the hepadnaviridae family, as well as other viruses causing acute and/or chronic hepatitis, like hepatitis delta virus, and hepatitis E virus.

The epitope prediction algorithm of the present invention is also suitable for the identification of amino acid sequences which are likely to induce an immune response in humans or animals against protein expressed by non-viral pathogens including bacteria, fungi, parasites pathogens For example, the algorithm disclosed herein can be used to identify epitopes for use in vaccines designed to confer immunity to non-viral pathogens, such as, but not limited to,: *Staphylococcus aureus, Streptococcus pyogenes, Streptococcus pneumoniae, Vibrio cholerae, Clostridium tetani, Neisseria meningitis, Corynebacterium diphteriae, Mycobacteria tuberculosis* and *leprae, Listeria monocytogenes*, and *Legionella pneumofila*. Examples of fungi and mammalian parasites for which it may be desirable to prepare prophylactic or therapeutic vaccines include: *Candida albicans, Aspergillus fumigatus, Histoplasma capsulatum, Plasmodium malariae, Leishmania major, Trypanosome cruzi* and *brucei, Schistosoma haematobium, mansoni* and *japonicum; Entamoeba histolytica*, and numerous species of *Filaria* known to be responsible for human filariasis.

Cancer typically involves the deregulation of genes that encode polypeptides which contribute to maintaining cell cycle or controlling cell proliferation (e.g., growth factors, oncogenes, receptors and tumor suppressors). The products of many of the genes implicated in cancer are expressed on the surface of a wide variety of tumor cells. A variety of tumor antigens that may be recognized by T and B lymphocytes have been identified in human and animal cancer. The vast majority of human tumor-associated antigens (TAAs) that are suitable for use in an anticancer vaccine trial are described as "self-antigens" due to the fact that in addition to being expressed on tumor cells they also are expressed on normal tissue and/or during fetal development. Immune tolerance of the target population to TAAs may explain why many cancer vaccines have proven to be ineffective.

Accordingly, if the epitope identification algorithm of the invention is being employed to select epitopes for use in a cancer vaccine, suitable amino acid sequences can be obtained from proteins which represent aberrantly expressed self-antigens, such as a tumor associated antigen (TAA). In the case of peptide sequences derived from aberrant self-antigens, suitable sequences included epitopes which can elicit an immune response which is sufficient to both break host tolerance to the TAA, and to elicit a long-lived (e.g., memory) response that will be sufficient to prevent the initiation of cancer or to prevent tumor progression Tumor-associated antigens finding advantageous use in the present invention may generally be selected from among protein products of oncogenes, tumor suppressor genes and other genes with mutations or rearrangements unique to tumor cells, reactivated embryonic gene products (e.g. oncofetal antigens), tissue-specific differentiation antigens, growth factor receptors, cell surface carbohydrate residues, foreign viral proteins and a number of other self proteins.

Tumor antigens can be produced by oncogenic mutants of normal cellular genes altered proto-oncogenes or tumor suppressor genes such as Ras, p53 or Bcr-Abl protein are examples of altered cellular proteins that can stimulate T/B cell response. Tumor antigens can be normal cellular proteins that are overexpressed in tumor cells (tyrosinase, GP100, MART are normally expressed at low levels in melanocytes and overexpressed in melanoma) or aberrantly expressed in tumor cells (MAGE, BAGE, GAGE expressed in melanomas and many carcinomas but normally expressed in the testis and placenta). Tumor antigens can be products of oncogenic viruses: papillomavirus E6 and E7 proteins expressed by cervical carcinomas; EBV EBNA-1 protein produced by EBV+lymphomas and nasopharyngeal carcinomas; SV40 T antigen in SV40 induced experimental tumors. Oncofetal antigens are expressed to high levels on cancer cells and in normal developing (fetal) tissues but not in adult tissues. Carcinoembryonic antigen (CEA) and alpha-fetoprotein (AFP) are examples of well characterized oncofetal antigens.

Recent evidence supports the existence of TAAs that are capable of eliciting an immune response, thus making this class of antigens suitable immunogens for vaccine therapy. However, as a class of antigens TAAs are notoriously poor immunogens and T-cells that are highly specific for TAAs are either deleted or anergized during T-cell development. Accordingly, there is an expectation that the immune response of a tumor-bearing host to a particular TAA will be extremely weak. Because of the inherent need to break host tolerance to a target TAA experimental clinical vaccine studies are particularly focused on developing immunization strategies that will enhance TAA-specific T-cell responses.

Generally speaking, an effective cancer vaccine must both overcome immune tolerance and enhance host's immune response to a level that is preventative and/or protective. Anti-tumor effects in many experimental vaccine studies have been correlated with T-cell responses to TAAs. Cancer vaccines can be either prophylactic or therapeutic. The general assumption underlying the prophylactic use of cancer vaccines is that TAAs are extremely weak immunogens or functionally non-immunogenic in tumor-bearing subjects.

In an alternative embodiment, the invention contemplates use of the disclosed epitope identification algorithm to select peptide sequences for use in an immunogenic composition (e.g., a cancer vaccine) designed to induce an immune response against tumor antigens. Development of an effective cancer vaccine will require the identification of a strategy that will elicit antigen-specific immunity in vaccinated patients which persists after active immunization has ended. The success of the strategy will depend on whether a measurable immune response directed against a target antigen will correlate with protection against cancer occurrence or relapse.

Target antigens which are of particular interest are self-proteins derived from poorly immunogenic and non-immunogenic tumors, which present special challenges due to their failure to provide adequate antigenic stimulation to provoke an immune response. In these cases, a self antigen common to both normal and cancerous tissue can be targeted such as, e.g., a tissue-specific differentiation antigen. In this aspect of the invention, a cancer vaccine comprising a tumor-associated self antigen preparation is administered to a subject in order to break immune tolerance to the antigen and stimulate an autoreactive peripheral T-cell response against T-cells expressing the self antigen. In a particular embodiment of this aspect of the invention, it may be advantageous to utilize the binding filter of the invention in combination with the natural processing, self-similarity, and immunogenicity enhancement filters that are disclosed and claimed herein.

Data from experimental systems suggest that antigen-specific T-cells represent the most powerful immunologic mechanism for the elimination of tumor cells. Recognition of tumor-specific antigens (e.g., TAAs) by effector T-cells is predicted to allow the TAA to function as a tumor-rejection antigen. Published studies suggest that stimulation of CD8+ and CD4+ helper T-cell responses are important for achieving optimal tumor clearance (P. Greenberg, *Adv. Immunol* 1991, 49: 281-355; D. Pardoll et al., *Curr Opin Immunol* 1998, 10: 588-94). Clinical response (i.e., efficacy) has been associated with increases in interferon γ-secreting cytotoxic T-cells. The advent of assays, such as the ELISPOT assay, allows investigators to measure T-cell responses to vaccination regimens and thereby facilitates the development of cancer vaccines.

More specifically, in the field of cancer immunology, vaccines can be used as immunotherapy in patients afflicted with cancer. Accordingly, cancer vaccines can be designed to elicit an immune response that is that is directed against a TAA that is expressed by a pre-existing tumor or malignancy. Thus, in particular embodiments, therapeutic cancer vaccines are intended for use in tumor-bearing patients who have developed resistance to conventional regimens of treatment or who have a high probability of developing a recurrence following conventional treatment.

TAAs that are suitable for use in a cancer vaccine should possess a number of characteristics. For example, a target TAA must have a favorable expression profile, meaning that it should be preferentially expressed or overexpressed in the tumor or malignant tissue as compared with normal tissue. In addition, because TAAs that play a role in tumorigenesis are more likely to be retained during the different stages of cancer progression, a suitable target TAA should also preserved throughout tumor progression and metastases. Suitable target TAAs should also be expressed homogenously within the tumor. Third, suitable target TAAs must not be subject to absolute immunologic tolerance. More specifically, there should be some evidence that T-cells which can both recognize and respond to the TAA of interest have not been entirely deleted from the host's T-cell repertoire (N. Berinstein et al., *J Clin Oncol* 2002, 20: 2197-2207).

The disclosed epitope identification algorithm can also be used to identify TAA-derived peptide sequences which are predicted to be highly likely to bind to particular HLA class I allele. In one embodiment, the candidate epitope sequence represents a naturally occurring amino acid sequence which has been determined to have a binding score that is indicative of strong binding to the target MHC molecule. In an alternative embodiment, a set of candidate epitopes identified by the binding filter (i.e., epitope selection matrix) can be further classified by electing to optionally use the self-similarity filter of the invention in combination with the binding filter. Use of the self-similarity filter of the invention allows investigators to select candidate epitopes which are predicted have a low likelihood of eliciting an immune response that will be cross-reactive with other self proteins. In another alternative embodiment, the epitope(s) selected for use in a cancer vaccine may be an immunogenic analog of a naturally occurring peptide which has been optimized in a manner which is predicted to increase the immunogenicity of the peptide based on the data obtained by using the optimization filter of the invention. As noted above, the optimization filter disclosed herein can be used either alone, or in combination with the self-similarity and/or natural processing filters of the invention.

Carcinoembryonic antigen (CEA) has many characteristics which make it an attractive TAA for use as a target antigen for an anticancer vaccine. It is a member of the Ig superfamily which is characterized by a favorable expression pattern. It is expressed in more than 50% of all human cancers and has been implicated in the tumorigenesis process, which suggests that its expression may be selected and conserved throughout cancer progression. In addition, it has been established that immunologic tolerance to CEA is not absolute. Published studies establish that human T cells can recognize, become activated to, and lyse cancer cells that express CEA (N. Berinstein, J Clin Oncol 2002, 20: 2197-2207). For example, the immunization of patients with recombinant vaccinia virus expressing CEA, combined with subsequent peptide-based in vitro stimulations, generated CD8+ MHC-restricted CTLs capable of lysing autologous tumors (K. Tsang et al., *J Nat Cancer Inst* 1995, 87: 982-990). Alternatively, immunization of colorectal carcinoma patients after surgery with recombinant CEA was reported to induce weak antibody and cellular responses to recombinant CEA (A. Samanci et al., *Cancer Immunol Immunother* 1998, 47: 131-142). Further, the administration of anti-CEA anti-idiotypic antibody to patients diagnosed with colorectal cancer generated anti-CEA antibodies and idiotype-specific T-cell proliferation (L. Foon et al., *J Clin Invest* 1995, 96: 334-342). The literature also indicates that tolerance to CEA in cancer patients can be overcome with several different vaccination approaches (i.e., vaccination with recombinant CEA or recombinant orthopox or avipox-CEA viruses, administration of anti-idiotype antibodies, pulsing dendritic cells with CEA agonist epitopes).

CEA is an oncofetal glycoprotein that is expressed in normal fetal colon and to a much lesser extent in normal colonic mucosa. It is also overexpressed in the vast majority of adenocarcinomas, particularly those of the colon, pancreas, breast, lung, rectum and stomach. Many colorectal cancers and some carcinomas produce high levels of CEA that are measurable in sera, which makes it one of the most widely used serological markers of malignancy, especially in patients with colorectal cancer.

A second TAA which provides a suitable target antigen from which candidate epitopes can be selected for use in a multi-epitope cancer vaccine is the product of the HER2/erb-2 (also called neu) proto-oncogene. Like, CEA, HER2/neu has a favorable expression pattern and is not subject to absolute tolerance. More specifically, low levels of expression of the HER2/neu transcript, and the 185 kD polypeptide product, are detected in normal adult epithelial cells of various tissues, including the skin and breast, and tissues of the gastrointestinal, reproductive, and urinary tracts; higher levels of expression are detected in the corresponding fetal tissues during embryonic development (Press et al., *Oncogene* 5: 953-962 (1990). Several lines of evidence suggest a link between the amplification of HER-2 and neoplastic transformation in human breast, lung, prostate, ovarian, endometrial and colorectal tumors (Disis and Cheever, *Adv Cancer Research* 71: 343-371 (1997). Generally speaking, overexpression of HER2/neu correlates with a poor prognosis and a higher relapse rate for cancer patients (Slamon et al., *Science* 244: 707-712 (1989). Thus, a vaccine specific for the HER-2/neu protein could have wide application and utility in the prevention of disease recurrence in many different human malignancies.

HER2/neu encodes a transmembrane glycoprotein possessing intrinsic tyrosine kinase activity and displaying extensive homology to the epidermal growth factor (EGF) receptor (Akiyama, T et al., (1986) Science 232: 1644-1646). One of the first clinical studies which utilized HER2 as target for cancer immunotherapy employed the HER-2-specific monoclonal antibody Herceptin for the treatment of breast cancer (Goldenberg MM (1999) Clin. Ther. 21: 309-318). This led to subsequent efforts which focused on the use of HER-2 as a target for the T-cell arm of the immune system to elicit effective antitumor responses, including the use of recombinant fusion proteins comprising HER-2 domains to activate autologous antigen presenting cells. Published reports establish that numerous cancer patients afflicted with neu-expressing mammary and ovarian cancers mount immune responses (e.g., produce antigen-specific antibody and T-cells) against the protein product of the HER2/neu oncogene.

In practice the epitope identification algorithm of the invention can be used to design a multi-epitope cancer vaccine which may include epitopes derived from a combination of self-antigens such as: HER2/neu, CEA, Epcam, PSA, PSMA, Telomerase, gp100, Melan-A/MART-1, Muc-1, NY-ESO-1, Survivin, Stromelysin 3, Tyrosinase, MAGE3, CML68, CML66, OY-TES-1, SSX-2, SART-1, SART-2, SART-3, NY—CO-58, NY-BR-62, hKLP2, VEGF. Additional self antigens which represent suitable targets for use in a cancer vaccine are known to the skilled artisan and can be identified by methods well known in the art, such as expression cloning, to allow immunization against defined antigens of known distribution and provide a more focused immune response.

The disclosed methodology allows a scientist to rationally design microbial or tumor vaccines that minimize potential for off-target autoimmune activity, by selective modification and/or deletion from the vaccine candidate, those fragments that are identical or highly similar to fragments of other human proteins. Candidate T-cell epitopes identified using this invention can be used as part of a gene-, protein-, vector-, or cell-based immunogenic composition to treat or prevent an infectious disease or cancer. Identified T-cell epitopes can also be used as part of an assay to monitor and evaluate the cellular immune responses which are induced by a vaccine candidate. For example, an epitope, or an optimized analog of a naturally occurring epitope, can be used as the basis of an in vitro assay which is established to measure target antigen-specific cell-mediated immunity using lymphocytes obtained from an individual prior to and after immunization with an epitope vaccine comprising predicted T-cell epitopes.

The invention also provides an analytical method for identifying modifications in known, or predicted T-cell epitopes that could confer an analog with the ability to elicit a stronger cellular immune response due to more efficient processing and/or presentation to T-cells. It is contemplated that the use of an analog identified with the immunoenhancement in the context of a gene-, protein-, vector-, or cell-based immunogenic composition could elicit an enhanced immune response (compared to the unmodified wild-type epitope) which is cross-reactive with the target antigen. For example, data derived from the use of the disclosed immunoenhancement filter in combination with an allele-specific binding filter can be used to design a recombinant full-length immunoenhanced target antigen which incorporates one or more amino acid substitutions which are predicted to result in the generation of immunogenic T-cell epitopes in vivo.

It is contemplated that candidate T-cell epitopes identified, and optionally optimized, by the algorithm described herein can be incorporated into a genetic vaccine, in the context of a minigene encoding the epitopes as a "string-of-beads." Several laboratories have published reports documenting the use of constructs encoding as many as eleven epitopes to induce CTL, and B cell immune responses, which are restricted by murine MHC molecules. An expression construct comprising a minigene encoding a multiepitope minigene can be delivered in vivo by injection (e.g., intramuscular or intradermal) of purified DNA, by infection with a recombinant adenovirus or vaccinia.

Designing vaccines which are capable of inducing a broad immune response that is simultaneously directed against multiple epitopes appears to be a crucial consideration for the development of efficacious vaccines against several important diseases. For pathogens that are adept at evading their host's immune responses by mutation, such as Hepatitis C virus (HCV), hepatitis B virus (HBV), or Human Immunodeficiency virus (HIV), by mutation, it is advantageous to design a vaccine with the goal of inducing a vigorous CTL response against multiple highly conserved epitopes.

The simplest design for a multiepitope vaccine is the "string of beads" design in which a series of epitopes are linked to each other without any intervening spacer sequences. It is acknowledged that the efficiency by which multiepitope vaccines are processed can be optimized by the use of spacer residues which are designed to facilitate generation by the recipient's natural processing pathway. The epitopes selected for inclusion in an immunogenic composition can be derived from multiple target proteins of the same, or different pathogen or tumor cell, and may be selected to cover several known or predicted epitope variants which may have developed as a consequence of mutations adapted to escape CTL recognition.

A growing body of experimental evidence demonstrates that a number of different approaches are available which allow simultaneous delivery of multiple epitopes. A preferred means of administering multiepitope vaccines is to utilize a minigene construct which comprise a nucleic acid sequence encoding an amino acid sequence which comprises one or multiple epitopes. The use of multi-epitope minigenes is described below and in, e.g. An, L. and Whitton, J. L., J. Virol. 71:2292, 1997; Thomson, S. A. et al., J. Immunol. 157: 822, 1996; Whitton, J. L. et al., J. Virol. 67:348, 1993; Hanke, R. et al., Vaccine 16:426, 1998. For example, a multi-epitope DNA plasmid encoding nine dominant HLA-A*0201- and A11-restricted epitopes derived from the polymerase, envelope, and core proteins of HBV and HIV, the PADRE™ Universal helper T cell (HTL) epitope, and an ER-translocating signal sequence was engineered. Generally speaking, the primary objective when designing a minigene is to generate the smallest peptide possible that encompasses the selected T-cell epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that could be reverse translated and included in the minigene sequence include: HLA class I epitopes, HLA class II epitopes, a ubiquitination signal sequence, a leader sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression. In addition, immunostimulatory sequences (ISSs or CpGs) appear to play a role in the immunogenicity of DNA vaccines. These sequences may be included in the vector, outside the minigene coding sequence, if desired to enhance immunogenicity.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector are confirmed using restriction mapping and DNA sequence analysis. Bacterial cells harboring the correct plasmid can be stored as a master cell bank and a working cell bank.

Target cell sensitization can be used as a functional assay for expression and HLA class I presentation of minigene-encoded CTL epitopes, respectively. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates production of HLA presentation of minigene-encoded CTL epitopes.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, IP for lipid-complexed DNA). Twenty-one days after immunization, splenocytes are harvested and restimulated for 1 week in the presence of peptides encoding each epitope being tested. For CTL effector cells, assays are conducted for cytolysis of peptide-loaded, chromium-51 labeled target cells using standard techniques. Lysis of target cells sensitized by HLA loading of peptides corresponding to minigene-encoded epitopes demonstrates DNA vaccine function for in vivo induction of CTLs.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids can also be used in the formulation (see, e.g., as described by WO 93/24640; Mannino & Gould-Fogerite, *BioTechniques* 6(7): 682 (1988); U.S. Pat. No. 5,279,833; WO 91/06309; and Feigner, et al., *Proc. Nat'l Acad. Sci. USA* 84:7413 (1987). In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types. Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Depending upon the nature of the pathogen or cellular target which the vaccine is developed for, it may be advantageous to combine epitopes which are predicted to be both high- and low-affinity MHC class I binders in a single minigene construct. This consideration is particularly relevant in the context of a target antigen that contains dominant epitopes, which are known to vary in their binding affinities. The set of epitopes selected for inclusion in an immunogenic composition, can be optimized for natural processing, immunogenicity, uniqueness (e.g., lack of similarity to other self-antigens), population coverage, and predicted disease relevance.

A skilled artisan can easily identify and establish both in-vitro and in-vivo immunogenicity assays that are suitable to evaluate the efficacy of a proposed multiepitope vaccine. For example, HLA transgenic mice can be used to evaluate the immunogenicity of a composition based on epitopes identified with the epitope identification algorithm described herein.

Examples are provided below to further illustrate different features of the present invention. The examples also illustrate useful methodology for practicing the invention. It is to be understood that these examples are not intended to limit the scope of the claimed invention.

Any suitable materials and/or methods known to those of skill can be utilized in carrying out the present invention; however, preferred materials and/or methods are described. Materials, reagents and the like to which reference is made in the following examples are obtainable from commercial sources, unless otherwise noted. Sequence information for the peptides used to construct the training sets and the candidate T-cell epitopes were obtained from publicly available databases. It is believed that one skilled in the art can, based on the description herein, utilize the present invention to its fullest extent. The entire contents of all of the references (including literature references, issued patents, published patent applications, and co-pending patent applications) cited throughout this application are hereby expressly incorporated by reference.

Example 1

Derivation of a Bayes-Corrected Scoring Matrix From Binding Data For the Murine Class I Molecule H-2K$^d$ This example illustrates how the methodology of the disclosed invention is used to derive a Bayes-corrected scoring matrix for the murine MHC Class I allele H-2K$^d$.

Step 1: Identify Strong Binders to H-2K$^d$

As of Jan. 30, 2005, 51 (fifty one) unique strong binders to H-2K$^d$ were available from the aforementioned epitope databases (Jenpep, MHCBN, and FIMM). The peptides were obtained by selecting the option "Report strong binders to H-2K$^d$", in each of the three databases. The identified peptides are listed in Table 1 (SEQ ID NOS.: 90-99 (8 mers), SEQ ID NOS.: 1-38 (9 and 10 mers), SEQ ID NO.: 100 (11 mer), SEQ ID NO.: 101 (12 mer), and SEQ ID NO.: 102 (13 mer), respectively). Thirty eight (38) of the strong binders were 9-mers and 10-mers (SEQ ID NOS.: 1-38) and were retained for further analysis. The other 13 peptides reported in the databases were of lengths shorter than 9 amino acid residues (SEQ ID NOS.: 90-99) or longer than 10 residues (100-102) and were excluded from the training set.

TABLE 1

H2-K$^d$ Strong Binders

| Peptide | Length |
|---|---|
| AIINFEKL | 8 |
| RGYVYQGL | 8 |
| SAINFEKL | 8 |
| SIIAFEKL | 8 |
| SIINFAKL | 8 |
| SIINFEAL | 8 |
| SIINFEKL | 8 |
| YIPAAEKI | 8 |
| YIPLAEKI | 8 |
| YIPNAEKI | 8 |
| APHFMPTNL | 9 |
| DYEELREQL | 9 |
| FAPGNYPAL | 9 |
| FYIQMCTEL | 9 |
| IHGVGALL | 9 |
| IYSTVASSL | 9 |
| KYQAVTTTL | 9 |
| LRGYVYQGL | 9 |
| LYEKVKSQL | 9 |
| RGYVYQGLK | 9 |
| SFAVATTAL | 9 |
| SIINFEKLT | 9 |
| SYETFISRL | 9 |
| SYIPAAEKI | 9 |
| SYIPIAEKI | 9 |
| SYIPLAEKI | 9 |
| SYIPNAEKI | 9 |
| SYVPSAEQI | 9 |

TABLE 1-continued

H2-K$^d$ Strong Binders

| Peptide | Length |
|---|---|
| TYQRARALV | 9 |
| TYQRNRALV | 9 |
| TYQRTRALV | 9 |
| VYVDGANGV | 9 |
| YPAFMPTNL | 9 |
| YPHFMPTAL | 9 |
| YPHFMPTNL | 9 |
| AYLENGKETL | 10 |
| MYPHFMPTNL | 10 |
| RYLANGKETL | 10 |
| RYLEAGKETL | 10 |
| RYLENAKETL | 10 |
| RYLENGAETL | 10 |
| RYLENGKATL | 10 |
| RYLENGKEAL | 10 |
| RYLENGKETL | 10 |
| RYLKAGKETL | 10 |
| RYPHFMPTNL | 10 |
| SIINFEKLTE | 10 |
| YFIFIGVGAL | 10 |
| TYQRTRALVTG | 11 |
| TYQRTRALVTTG | 12 |
| ISTQNHRALDLVA | 13 |

Step 2: Cluster the Selected Peptides

Clustering this data at the 65% sequence identity threshold resulted in 20 distinct clusters. The peptides and the clusters into which they were assigned are summarized in Table 2.

TABLE 2

H2-K$^d$ Strong Binder Peptide Clusters

| Peptide | Cluster ID | SEQ ID NO: |
|---|---|---|
| APHFMPTNL | 1 | 1 |
| YPAFMPTNL | 1 | 23 |
| YPHFMPTAL | 1 | 24 |
| YPHFMPTNL | 1 | 25 |
| DYEELREQL | 2 | 2 |
| FAPGNYPAL | 3 | 3 |
| FYIQMCTEL | 4 | 4 |

TABLE 2-continued

H2-K$^d$ Strong Binder Peptide Clusters

| Peptide | Cluster ID | SEQ ID NO: |
|---|---|---|
| IFIGVGALL | 5 | 5 |
| IYSTVASSL | 6 | 6 |
| KYQAVTTTL | 7 | 7 |
| LRGYVYQGL | 8 | 8 |
| LYEKVKSQL | 9 | 9 |
| RGYVYQGLK | 10 | 10 |
| SFAVATTAL | 11 | 11 |
| SIINFEKLT | 12 | 12 |
| SYETFISRL | 13 | 13 |
| SYIPAAEKI | 14 | 14 |
| SYIPIAEKI | 14 | 15 |
| SYIPLAEKI | 14 | 16 |
| SYIPNAEKI | 14 | 17 |
| SYVPSAEQI | 14 | 18 |
| TYQRARALV | 15 | 19 |
| TYQRNRALV | 15 | 20 |
| TYQRTRALV | 15 | 21 |
| VYVDGANGV | 16 | 22 |
| AYLENGKETL | 17 | 26 |
| RYLANGKETL | 17 | 28 |
| RYLEAGKETL | 17 | 29 |
| RYLENAKETL | 17 | 30 |
| RYLENGAETL | 17 | 31 |
| RYLENGKATL | 17 | 32 |
| RYLENGKEAL | 17 | 33 |
| RYLENGKETL | 17 | 34 |
| RYLKAGKETL | 17 | 35 |
| MYPHFMPTNL | 18 | 27 |
| RYPHFMPTNL | 18 | 36 |
| SIINFEKLTE | 19 | 37 |
| YFIFIGVGAL | 20 | 38 |

Step 3: Compute Empirical Scoring Function

Formula (2) is used to compute the empirical scoring function F. Specifically, for each amino acid and at each position, we calculated the fraction of clusters that contain the amino acid at that position. The empirical scoring function F resulting from these calculations is presented in Table 3.

TABLE 3

Empirical Scoring Function, F, as computed by formula (2)

| | 1 | 2 | 3 | 4 | 5 | 6 | 7 | 8 | 9 |
|---|---|---|---|---|---|---|---|---|---|
| A | 0.1 | 0.05 | 0.1 | 0.1 | 0.2 | 0.2 | 0.15 | 0.25 | 0 |
| C | 0 | 0 | 0 | 0 | 0 | 0.05 | 0 | 0 | 0 |
| D | 0.05 | 0 | 0 | 0.05 | 0 | 0 | 0 | 0 | 0 |
| E | 0 | 0 | 0.15 | 0.1 | 0.05 | 0.05 | 0.15 | 0.05 | 0.05 |
| F | 0.1 | 0.15 | 0 | 0.1 | 0.2 | 0 | 0 | 0 | 0 |
| G | 0 | 0.05 | 0.05 | 0.1 | 0.15 | 0.05 | 0.1 | 0.1 | 0 |
| H | 0 | 0 | 0.05 | 0.05 | 0 | 0 | 0 | 0 | 0 |
| I | 0.1 | 0.1 | 0.3 | 0 | 0.1 | 0.05 | 0 | 0 | 0.05 |
| K | 0.05 | 0 | 0 | 0.1 | 0 | 0.15 | 0.05 | 0.05 | 0.05 |
| L | 0.1 | 0 | 0.05 | 0 | 0.1 | 0 | 0.05 | 0.2 | 0.7 |
| M | 0.05 | 0 | 0 | 0 | 0.15 | 0 | 0 | 0 | 0 |
| N | 0 | 0 | 0 | 0.1 | 0.2 | 0 | 0.05 | 0.1 | 0 |
| P | 0 | 0.05 | 0.1 | 0.05 | 0 | 0.1 | 0.05 | 0 | 0 |
| Q | 0 | 0 | 0.1 | 0.05 | 0 | 0.05 | 0.05 | 0.15 | 0 |
| R | 0.15 | 0.05 | 0 | 0.05 | 0 | 0.1 | 0 | 0.05 | 0 |
| S | 0.25 | 0 | 0.05 | 0 | 0.05 | 0 | 0.15 | 0.05 | 0 |
| T | 0.05 | 0 | 0 | 0.1 | 0.05 | 0.1 | 0.25 | 0.15 | 0.05 |
| V | 0.05 | 0 | 0.1 | 0.1 | 0.25 | 0.05 | 0 | 0 | 0.1 |
| W | 0 | 0 | 0 | 0 | 0 | 0 | 0 | 0 | 0 |
| Y | 0.1 | 0.55 | 0.05 | 0.05 | 0.05 | 0.1 | 0 | 0 | 0 |

To illustrate the difference between the empirical scoring function formula presented in (2) and the "frequency of occurrence" approach (1) which is the standard in the art, consider the occurrence of leucine (L) in position 3. L occurs 9 times among the 38 peptides in this dataset; hence its frequency of occurrence is 9/38, or 24.7%. Note however, that all the occurrences of leucine in position 3 are in the context of a single cluster (#17), composed of highly similar peptides. Using (2), the empirical score of leucine at position 3 is 1/20, or 5%. Since the peptides in cluster 17 are derived from a single peptide and thus only constitute evidence for a single occurrence of leucine, the standard approach overstates the preference of K$^d$ for leucine at pos 3 by a factor of 5.

Step 4: Compute Bayes-corrected Scoring Matrix

A Bayes-corrected scoring matrix B is computed from F (the Empirical Scoring Function) using the formula (4) and is presented in Table 4.

TABLE 4

Bayes-corrected Scoring Function, B, as computed by formula (4)

| | 1 | 2 | 3 | 4 | 5 | 6 | 7 | 8 | 9 |
|---|---|---|---|---|---|---|---|---|---|
| A | 0.17 | −0.27 | 0.17 | 0.17 | 0.72 | 0.72 | 0.48 | 0.91 | −1.10 |
| C | −1.10 | −1.10 | −1.10 | −1.10 | −1.10 | 0.90 | −1.10 | −1.10 | −1.10 |
| D | −0.04 | −1.10 | −1.10 | −0.04 | −1.10 | −1.10 | −1.10 | −1.10 | −1.10 |
| E | −1.10 | −1.10 | 0.62 | 0.30 | −0.18 | −0.18 | 0.62 | −0.18 | −0.18 |
| F | 0.69 | 1.03 | −1.10 | 0.69 | 1.29 | −1.10 | −1.10 | −1.10 | −1.10 |
| G | −1.10 | −0.21 | −0.21 | 0.26 | 0.57 | −0.21 | 0.26 | 0.26 | −1.10 |
| H | −1.10 | −1.10 | 0.59 | 0.59 | −1.10 | −1.10 | −1.10 | −1.10 | −1.10 |
| I | 0.38 | 0.38 | 1.31 | −1.10 | 0.38 | −1.10 | −1.10 | −1.10 | −0.11 |
| K | −0.11 | −1.10 | −1.10 | 0.38 | −1.10 | 0.70 | −0.11 | −0.11 | −0.11 |
| L | 0.03 | −1.10 | −0.38 | −1.10 | 0.03 | −1.10 | −0.38 | 0.54 | 1.65 |
| M | 0.55 | −1.10 | −1.10 | −1.10 | 1.51 | −1.10 | −1.10 | −1.10 | −1.10 |
| N | −1.10 | −1.10 | −1.10 | 0.65 | 1.25 | −1.10 | 0.11 | 0.65 | −1.10 |
| P | −1.10 | 0.02 | 0.54 | 0.02 | −1.10 | 0.54 | 0.02 | −1.10 | −1.10 |
| Q | −1.10 | −1.10 | 0.71 | 0.17 | −1.10 | 0.17 | 0.17 | 1.06 | −1.10 |
| R | 0.80 | −0.03 | −1.10 | −0.03 | −1.10 | 0.47 | −1.10 | −0.03 | −1.10 |
| S | 1.01 | −1.10 | −0.20 | −1.10 | −0.20 | −1.10 | 0.58 | −0.20 | −1.10 |
| T | −0.06 | −1.10 | −1.10 | 0.44 | −0.06 | 0.44 | 1.22 | 0.77 | −0.06 |
| V | −0.19 | −1.10 | 0.28 | 0.28 | 1.04 | −0.19 | −1.10 | −1.10 | 0.28 |
| W | −1.10 | −1.10 | −1.10 | −1.10 | −1.10 | −1.10 | −1.10 | −1.10 | −1.10 |
| Y | 0.91 | 2.50 | 0.34 | 0.34 | 0.34 | 0.91 | −1.10 | −1.10 | −1.10 |

Example 2

Use of a Bayes-corrected scoring matrix to Score Candidate Peptides

Step 1: Define Candidate Peptides of Target Protein

All possible 9mer and 10-mer frames (longer and shorter frames are not considered because most binders to Class I HLA molecules are of length 9 to 10) are determined in silico from the amino acid sequence of a target protein of interest.

Step 2: Score and Rank Candidate Peptides

Score each fragment using BSM as follows:

For each 9-mer $a_1, \ldots a_9$, its score is obtained by simply adding the appropriate entries of the BSM:

$$S(a_1 \cdots a_9) = \sum_{i=1\ldots 9} B(a_i, i)$$

For each 10-mer $a_1 \ldots a_{10}$, its score is obtained by adding the scores of the 8 flanking amino acids and the average of the scores of the middle two positions:

$$S(a_1 \cdots a_{10}) = \sum_{i=1\ldots 4} B(a_i, i) + \sum_{i=7\ldots 10} B(a_i, i-1) + \frac{B(a_5, 5) + B(a_6, 5)}{2}$$

The output of binding affinity filter is a list of 9-mer and 10-mer peptide fragments ranked by their scores.

Example 3

T-cell Epitope Discovery in HCV-1

To validate the binding affinity filter described in this invention, we obtained 12 (twelve) published A2-restricted epitopes from the HCV virus from [P. Scognamiglio et al., *J Immunol* 1999, 162: 6681-6689]. The binding affinity of each epitope to the HLA-A2 was measured in a standard competitive inhibition assay against a radiolabeled probe peptide (see detailed protocol in the above-referenced paper). The epitopes (SEQ ID NOS.: 39-50, respectively) and their IC50 values are shown in Table 5.

TABLE 5

HLA-A2-restricted HCV epitopes from
P. Scognamiglio et.al., J Immunol. 1999, 162:
6681-6689.

| Peptide | Binding Affinity (IC50, nM) |
|---|---|
| DLMGYIPLV | 80.0 |
| YLVAYQATV | 20.4 |
| ILAGYGAGV | 116.3 |
| YLLPRRGPRL | 125.0 |
| VLVGGVLAA | 185.2 |
| FLLLADARV | 18.2 |
| LLFNILGGWV | 4.2 |
| RLIVFPDLGV | 56.2 |
| HMWNFISGI | 15.2 |
| YLVTRHADV | 454.5 |
| LLFLLLADA | 217.4 |
| WMNRLIAFA | 122.0 |

Separately, we derived a Bayes-corrected scoring matrix for HLA-A2 from a set of 289 unique, naturally occurring strong binders, following the data extraction and computation protocols described in Example 1 and the section on binding affinity filter (including the selection of epitope databases, criteria for selection of strong binders, clustering threshold, etc.) The resulting HLA-A2 Bayes-corrected scoring matrix is shown in Table 6.

TABLE 6

Bayes-corrected scoring matrix corresponding to HLA allele HLA-A2.

| | 1 | 2 | 3 | 4 | 5 | 6 | 7 | 8 | 9 |
|---|---|---|---|---|---|---|---|---|---|
| A | 0.16 | −1.73 | 0.04 | −0.03 | −0.19 | −1.16 | 0.2 | −0.06 | −0.31 |
| C | −0.73 | −3.32 | 0.32 | −0.33 | −0.53 | 0.83 | −0.07 | −0.08 | −0.71 |
| D | −1.19 | −2.26 | 0.46 | 0.7 | −0.44 | −0.02 | −1.44 | −1.2 | −3.33 |
| E | −1.62 | −3.32 | −1.38 | 0.46 | −0.35 | −0.75 | −0.46 | 0.23 | −3.33 |
| F | 0.58 | −2.07 | 0.76 | −0.93 | 0.61 | 0.01 | 0.42 | 0.15 | −3.33 |
| G | 0.11 | −2.42 | −0.28 | 0.73 | 0.57 | −0.42 | −0.7 | 0.26 | −2.43 |
| H | −0.41 | −3.32 | −0.02 | −1.03 | 0.29 | −1.04 | 0.65 | 0.46 | −3.33 |
| I | 0.05 | 0.41 | 0.05 | −0.35 | 0.02 | 0.74 | 0.26 | −0.47 | 0.4 |
| K | −0.08 | −2.33 | −1.87 | −0.65 | −0.2 | −0.93 | −1.87 | −0.23 | −1.86 |
| L | 0.23 | 1.97 | 0.26 | −0.45 | −0.27 | 0.49 | 0.39 | 0.02 | 1.17 |
| M | 0.42 | 1.03 | 0.32 | −0.71 | −1.28 | 0.43 | 0.32 | −0.08 | −0.71 |
| N | −0.8 | −3.32 | −0.05 | 0.13 | 0.06 | −0.14 | −0.24 | −0.16 | −3.33 |
| P | −1.12 | −3.32 | −0.37 | 0.75 | 0.06 | −0.17 | 0.3 | −0.76 | −3.33 |
| Q | −0.4 | −3.32 | −0.27 | 0.13 | −0.15 | −0.15 | 0.12 | 0.32 | −3.33 |
| R | 0.11 | −3.32 | −0.98 | −0.32 | −0.14 | −1.43 | −0.98 | 0.16 | −3.33 |
| S | 0.62 | −2.43 | −0.22 | 0.02 | −0.62 | −0.22 | −0.43 | 0.29 | −3.33 |
| T | −0.3 | −0.7 | −0.39 | −0.37 | 0.04 | 0.07 | −0.06 | 0.36 | −1.22 |
| V | 0.18 | 0.12 | 0.35 | −0.88 | 0.37 | 0.8 | 0.52 | −0.79 | 1.97 |
| W | −0.46 | −3.32 | 1.29 | 0.23 | 0.42 | −0.44 | 1.11 | 0.59 | −3.33 |
| Y | 0.62 | −3.32 | 0.56 | −1.88 | 0.37 | −0.17 | −0.05 | 0.24 | −3.33 |

Following the protocol described in Example 2 and the disclosed scoring techniques, the 12 HCV epitopes (SEQ ID NOS.: 39-50), listed in Table 5 the Bayes corrected HLA-A2 scoring matrix provided in Table 6, binding scores and percentiles were determined for the 12 HCV epitopes listed in Table 7. The percentile corresponding to a score x. We conclude that 11/12 HCV epitopes have scores higher than 95% of randomly generated peptides.

TABLE 7

Comparison of binding affinity and predicted binding score of published HLA-A2-restricted HCV epitopes.

| Peptide | Binding Affinity (IC50, nM) | Binding Filter Score | Percentile |
|---|---|---|---|
| DLMGYIPLV | 80.0 | 5.23 | 100.00 |
| YLVAYQATV | 20.4 | 5.66 | 99.98 |
| ILAGYGAGV | 116.3 | 5.17 | 99.94 |
| YLLPRRGPRL | 125.0 | 4.67 | 99.87 |
| VLVGGVLAA | 185.2 | 4.62 | 99.86 |
| FLLLADARV | 18.2 | 4.48 | 99.82 |
| LLFNILGGWV | 4.2 | 4.41 | 99.81 |
| RLIVFPDLGV | 56.2 | 4.18 | 99.74 |
| HMWNFISGI | 15.2 | 3.62 | 99.48 |
| YLVTRHADV | 454.5 | 2.36 | 98.33 |
| LLFLLLADA | 217.4 | 1.42 | 96.71 |
| WMNRLIAFA | 122.0 | 0.71 | 94.89 |

Generally speaking, peptides with scores in the highest percentile range are considered to be strong binders. The selection of a score or a percentile cutoff value usually depends on the capacity to carry out follow-on experimental studies to determine binding affinity and/or immunogenicity. For example, an artisan may choose all peptides in the 95$^{th}$ percentile or higher (or, 90$^{th}$ percentile or higher) range as candidate epitopes.

Example 4

T-cell Epitope Discovery in HIV-1

As a further validation experiment, we used HLA-A2 Bayes-corrected scoring matrix from Table 6, to score 18 (eighteen) published A2-restricted HIV-1 epitopes (SEQ ID NOS.: 51-68, respectively) mined from the LANL HIV Immunology database [Bette T. M et. al., Eds, *HIV Molecular Immunology* 2002, Los Alamos National Laboratory, Theoretical Biology and Biophysics, Los Alamos, N. Mex. LA-UR 03-5816] (http://hiv-web.lanl.gov/content/immunology/index). The epitopes and their scores and percentiles are shown in Table 8. It can be seen that 14 out of 18 published HLA-A2-restricted HIV-1 epitopes score in the top 5% of all peptides.

TABLE 8

Prediction of HIV-1 T-cell Epitopes

| HIV-1 Epitopes | Binding Score | Percentile |
|---|---|---|
| SLYNTVATL | 5.85 | 99.98 |
| KLTPLCVSL | 4.79 | 99.88 |
| VLAEAMSQV | 4.75 | 99.88 |
| ILKEPVHGV | 4.35 | 99.78 |
| SLLNATAIAV | 3.91 | 99.65 |
| RLRDLLLIV | 3.91 | 99.61 |
| LLWKGEGAV | 3.87 | 99.59 |
| ALVEICTEM | 3.25 | 99.22 |
| LLNATAIAV | 3.17 | 99.16 |
| QMHEDIISL | 3.09 | 99.10 |
| AIIRILQQL | 2.42 | 98.39 |
| RILQQLLFI | 2.19 | 98.06 |
| EILKEPVHGV | 1.94 | 97.73 |
| LVGPTPVNI | 1.45 | 96.73 |
| VIYQYMDDL | 0.61 | 94.51 |
| YQYMDDLYV | -0.71 | 88.66 |
| RGPGRAFVTI | -0.83 | 88.13 |
| IYQYMDDLYV | -3.70 | 61.80 |

Example 5

The Self-Similarity Filter can be Used to Identify Peptides which are not Unique to the Target Antigen The candidate peptide LVHPQWVLTA (SEQ ID NO: 83), which represents a fragment of the prostate specific antigen PSA (SwissProt accession number: P07288) (SEQ ID NO: 70) starting at position 54 (denoted as PSA.54) is predicted to bind to HLA Class I allele A*0201. The disclosed binding filter indicates that the peptide has a binding score of 2.46 (percentile=98.49%). However, information resulting from the use of the disclosed self-similarity filter indicates that the peptide is not unique to the target antigen, and as a result should not be considered for use in an immunogenic composition. In fact, a search of the SwissProt database using any of the search tools mentioned in the section on self-similarity filter, reveals that a 9-mer fragment (Tryptase delta 63) (SEQ ID NO: 71) that begins at position 63 of the human protein Tryptase delta (SwissProt accession no. Q9BZJ3) (SEQ ID NO: 72) is identical to PSA.54 except at position 2, which is an WIC contact position.

| LVHPQWVLTA PSA.54 | (SEQ ID NO:83) |
|---|---|
| LIHPQWVLTA Tryptase delta.63 | (SEQ ID NO:71) |

Accordingly, use of the disclosed self-similarity filter in combination with the binding filter, would cause an investigator to reject PSA.54 as a candidate T-cell epitope for use in a prostate cancer vaccine, despite its predicted strong binding to A*0201.

Example 6

Use of the Natural Processing Filter to Identify T-Cell Epitopes which are Unlikely to be Presented to T-cells Due to Impaired Cellular Processing Two fragments (i.e., peptides) of the Epstein-Barr virus, EBNA 3C.881 (QPRAPIRPI) (SEQ ID NO: 73) and EBNA 3A.379 (RPPIFIRRL) (SEQ ID NO: 74) both have a typical HLA-B7 binding motif comprising a proline position 2 and an aliphatic amino acid at the C-terminus. The binding filter of the invention predicts a HLA-B7 binding score of 2.08 for the EBNA 3C peptide and 1.93 for the EBNA 3A peptide. However, based on data produced in an ELISPOT assay measuring reactivity of PBMC-derived CTLs against the two peptides it been reported that only EBNA 3A.379 is recognized by memory T-cells isolated from HLA-B7-positive EBV-seropositive individuals (PNAS 1999, 96: 12033-12038).

The finding that the EBNA 3A fragment is immunogenic while higher-scoring EBNA 3C fragment is not would not be expected from a consideration of the binding scores alone. However, this outcome is consistent with the observation that the amino acid residue adjacent to the N-terminus of the EBNA 3C peptide is a proline residue. As shown herein, proline in position P1' is indicative of a peptide that is unlikely to be naturally processed. In contrast, the residue at the N-terminus of the EBNA 3A fragment is a lysine which does not have a similar association. Analysis of these two peptides using a combination of the disclosed binding filter and natural processing filter would result in a curated list of candidate peptides in which the EBNA 3A fragment, but not the EBNA 3C fragment, would be suggested as an immunogenic fragment. The EBNA 3 C peptide would be eliminated from the list because the natural processing filter would operate to reject it from a list of candidate T-cell epitopes.

This example illustrates how the natural processing filter of the invention operates to identify peptides which, based on the binding score alone, appear to be good T-cell candidates, yet are likely to be non-immunogenic in-vivo due to improper cellular processing.

Example 7

Use of the Binding Filter in Combination with the Self-Similarity and Natural Processing Filters to Identify and Rank Candidate T-cell Epitopes We applied the epitope identification algorithm disclosed herein to identify T-cell epitope candidates derived from the tumor-associated antigen PSA (SwissProt accession Number: P07288) (SEQ ID NO: 75). The sequence of this protein is as follows:

```
MWVPVVFLTSSVTWIGAAPLILSRIVGGWECEKHSQPWQVLVASRGRAVC

GGVLVHPQWVLTAAHCIRNKSVILLGRHSLFHPEDTGQVFQVSHSFPHPL

YDMSLLKNRFLRPGDDSSHDLMLLRLSEPAELTDAVKVMDLPTQEPALGT

TCYASGWGSIEPEEFLTPKKLQCVDLHVISNDVCAQVHPQKVTKFMLCAG

RWTGGKSTCSGDSGGPLVCNGVLQGITSWGSEPCALPERPSLYTKVVHYR

KWIKDTIVANP
```

Using the above-described binding affinity filter based on the HLA allele A*0201 as shown in Table 6, we determined binding scores for all 253 9-mers and 252 10-mers generated in silico from the PSA sequence. Based on the predicted binding scores, the ten (10) peptides having the highest predicted binding affinity were selected for further processing. Table 9 provides a list of the peptides, (SEQ ID NOS.: 76-85, respectively), their binding scores, and their positions in the target protein.

Three of the ten (VLVHPQWVL, SEQ ID NO: 79, LVHPQWVLTA, SEQ ID NO: 83, and GVLVHPQWV, SEQ ID NO: 84) are rejected based on a high degree of similarity to a fragment of another human protein.

A fourth peptide (PSA.217)(LVCNGVLQGI, SEQ ID NO: 82) which passed the self-similarity filter was rejected by natural processing filter.

Six of the peptides (FLTPKKLQCV, SEQ ID NO: 76; KLQCVDLHV, SEQ ID NO: 77; VISNDVCAQV, SEQ ID NO: 78; FLTLSVTWI, SEQ ID NO: 80; VLVASRGRAV, SEQ ID NO: 81 and KLQCVDLHVI SEQ ID NO: 85) were identified as candidate T-cell epitopes.

The data provided in Table 9 includes two candidate A*0201-restricted PSA T-cell epitopes (PSA.165 and PSA.178) (SEQ ID NO.: 76 and 78) which have been previously reported in the literature as PSA T-cell epitopes (P. Correale et. al., *J Natl Cancer Inst* 1997, 89: 293-300).

TABLE 9

| | | Predicted PSA T-cell Epitopes | | | |
|---|---|---|---|---|---|
| Binding Score | Peptide Sequence (SEQ ID NO) | Position in protein | Self-Similarity Filter | Natural Processing Filter | Immunogenic Analog (SEQ ID NO.) |
| 5.21 | FLTPKKLQCV (76) | 165 | Pass | pass | None |
| 4.46 | KLQCVDLHV (77) | 170 | Pass | pass | None |

TABLE 9-continued

Predicted PSA T-cell Epitopes

| Binding Score | Peptide Sequence (SEQ ID NO) | Position in protein | Self-Similarity Filter | Natural Processing Filter | Immunogenic Analog (SEQ ID NO.) |
|---|---|---|---|---|---|
| 3.79 | VISNDVCAQV (78) | 178 | Pass | pass | VLSNDVCAQV (86) |
| 2.87 | VLVHPQWVL (79) | 53 | Fail | pass | VLVHPQWVV (105) |
| 2.82 | FLTLSVTWI (80) | 7 | Pass | pass | FLTLSVTWV (87) |
| 2.60 | VLVASRGRAV (81) | 40 | Pass | pass | None |
| 2.54 | LVCNGVLQGI (82) | 217 | Pass | fail | LLCNGVLQGI (106) |
| 2.46 | LVHPQWVLTA (83) | 54 | Fail | fail | LVHPQWVLTV (69) |
| 2.41 | GVLVHPQWV (84) | 52 | Fail | pass | GLLVHPQWV (107) |
| 2.00 | KLQCVDLHVI (85) | 170 | Pass | pass | KLQCVDLHVV (88) |

Example 8

Use of the Immunoenhancement Filter of the Invention to Identify Immunogenic Analogs of Candidate T-cell Epitopes As disclosed herein the immunoenhancement filter of the invention can be used either in combination with the binding filter, self-similarity, and natural processing filters of the invention, or as a stand-alone tool to optimize candidate T-cell epitopes. Briefly, fixed anchor immunogenic analogs of candidate T-cell epitopes can be identified as follows:

(1) T-cell epitopes restricted by the allele of interest are identified
(2) Fixed-anchor analogs of the predicted T-cell epitopes are computed
(3) The sequence of the antigen of interest is modified by replacing predicted T-cell epitopes with their immunogenic analogs.

One or more immunoenhanced class I restricted T-cell epitopes can be incorporated into an immunogenic composition for use as a multiepitope vaccine. Alternatively, an immunoenhanced version of a full-length target antigen can be designed based on the disclosed methodology by introducing amino acid substitutions into the parental wild-type sequence based on the amino acid sequence of immunoenhanced anchor-modified analogs which the disclosed EIA has predicted will produce an immunoenhanced class I restricted T-cell epitope. Among the six A*0201-restricted T-cell epitope candidates identified for PSA in Example 7, three (3) were amenable to immunogenic modifications. In particular, PSA.178, PSA.7 and PSA.170 (the 10-mer) can be immunoenhanced to VLSNDVCAQV (SEQ ID NO: 86), FLTLSVTWV (SEQ ID NO: 87), and KLQCVDLHVV (SEQ ID NO: 88), respectively (with residue modifications indicated in bold). Either the epitopes, or their analogs, or both could be tested for immunogenicity, and used in an epitope-, gene-, protein-, vector, or cell-based vaccine to elicit a cell mediated immune response against PSA-expressing tumor cells.

For example, an immunoenhanced version of PSA, which incorporates the modified sequences of the fixed anchor analogs of the two candidate PSA T-cell epitopes PSA.7 and PSA.170 (the 10-mer), would have the following sequence (SEQ ID NO: 89):

```
MWVPVVFLTLSVTWVGAAPLILSRIVGGWECEKHSQPWQVLVASRGRAVC
GGLLVHPQWVVTVAHCIRNKSVILLGRHSLFHPEDTGQVFQVSHSFPHPL
YDMSLLKNRFLRPGDDSSHDLMLLRLSEPAELTDAVKVMDLPTQEPALGT
TCYASGWGSIEPEEFLTPKKLQCVDLHVLSNDVCAQVHPQKVTKFMLCAG
RWTGGKSTCSGDSGGPLLCNGVLQGITSWGSEPCALPERPSLYTKVVHYR
KWIKDTIVANP.
```

Example 9

In Vitro Evaluation of the Binding Affinity of Candidate T Cell Epitopes Selected by the Epitope Identification Algorithm Prior to their inclusion in an immunogenic composition, peptides selected by the epitope identification/optimization algorithm of the invention could be further tested in vitro for their ability to bind to the appropriate HLA allele. A number of cell-free or cell-based assays to test binding affinity to the HLA molecule are used in the art and can be performed by a skilled artisan following published protocols. For example, the relative affinity of a candidate peptide for an HLA allele and peptide/MHC complex stability could be determined using on of the following assays:

1) "T2 assay": TAP-deficient T2 cells (e.g., 105-106/m1) expressing the appropriate HLA allele are incubated with various concentrations of the peptide (e.g., 0.1-100 uM) and β2m at room temperature. Peptide-induced MHC/peptide complexes are detected with a fluorescent-labeled antibody. Relative affinity is calculated as mean fluorescence of peptide-incubated T2-cells minus mean fluorescence of T2 cells incubated with a control peptide. The dissociation rate is measured as the time to achieve 50% reduction in the initial fluorescence. Details of the assay can be found in: A. Scardino, Eur J Immunol 2001, 31: 3261-3270.

2) iTopia binding assay. Here, unfolded HLA molecules are combined with various concentrations of the test peptide and β2m. Properly folded HLA/peptide complexes are detected using a fluorescent-labeled antibody. The relative affinity and dissociation rate are measured as in the T2 assay. Details of the iTopia assay can be found in: R. Raynor, Continuity of T-Cell vaccine Development from Design through Correlates of Immunity: Identification and Mapping of Immunogenic Epitopes, World Vaccine Congress 2003, http://www.immunomics.com/raynor1.asp.

Based on the disclosure provided herein, it is well within the skill of an investigator to identify other suitable assays for the in vitro determination/characterization of the binding affinity of candidate T-cell epitopes which are selected or identified by the disclosed epitope identification algorithm.

Example 10

In Vitro and In Vivo Evaluation of the Immunogenicity of Candidate T Cell Epitopes Selected by the Epitope Identification Algorithm Prior to their inclusion in a vaccine construct (i.e., minigene), the immunogenicity of polynucleotide sequences encoding a T-cell epitope selected by the disclosed methodology could be evaluated in vitro or in vivo. For example, the ability of a minigene to induce specific $CD8^+$ cells can be evaluated in an in vitro assay. A number of assays are used in the art for that purpose and can be performed by a skilled artisan following published protocols. For example, the immunogenicity of a candidate T-cell epitope selected or optimized according to the methodology disclosed herein could be assessed in one of the following assays (among others):

(1) In-vitro T-cell stimulation (IVS). Here, CTLs are extracted from healthy or diseased individuals and stimulated with autologous peptide-pulsed peripheral blood mononuclear cells (PBMC). After several (e.g., four) weekly restimulations, T-cells are tested for reactivity against the peptide using either HLA-matched, peptide-pulsed cells, or cells expressing the protein from which the peptide was derived. A detailed protocol can be found in: E. Keogh, *Identification of New Epitopes from Four Different Tumor-Associated Antigens: Recognition of Naturally Processed Epitopes Correlates with HLA-A\*0201-Binding Affinity*, J Immunol 2001, 167: 7870-796, the teachings of which are incorporated herein by reference.

(2) Immunization of transgenic mice. Here, mice transgenic for the allele of interest are injected with the peptide, with or without an adjuvant, in several (e.g., four) weekly injections. After the last injection, PBMCs from the immunized mice are tested in vitro for their ability to recognize HLA-matched, peptide-pulsed cells or HLA-matched cells expressing the protein from which the peptide was derived. A detailed description of the procedure can be found in: H. Firat, *H-2 Class I knockout, HLA-A2.1-transgenic mice: a versatile animal model for preclinical evaluation of anti-tumor immunotherapeutic strategies*, Eur J Immunol 1999, 29: 3112-3121.

Based on the disclosure provided herein, it is well within the skill of an investigator to identify other suitable assays for the in vitro determination/characterization of the immunogenicity of candidate T-cell epitopes which are selected or identified by the disclosed methodologies.

What is claimed is:

1. A computer-assisted method for identifying T-cell epitopes of a target protein that are likely to bind to an MHC class I allele of interest comprising:

a) selecting an MHC allele of interest;

b) collecting and curating a training set which comprises peptide sequences which are known to bind to the MHC allele, wherein the peptide sequences consist of 9 amino acid positions (9mers) or 10 amino acid positions (10mers);

c) grouping the peptide sequences in the training set into clusters based on a predetermined amino acid sequence identity threshold;

d) determining an empirical binding score matrix (ESM) which summarizes the fraction of clusters that contain each of 20 amino acids at each of the 9 or 10 positions of the peptide sequences in the training set; wherein the values of the ESM (F) are calculated:

(i) $F(i,j)=n(i,j)/N_j$ for flanking positions, j, wherein flanking positions are positions 1-4 and 6-9 for 9mers and positions 1-4 and 7-10 for 10mers, and (ii) $F(i,j)=\frac{1}{2}$(number of 9mer clusters containing i at position 5/total number of clusters of 9mers)+((number of 10mer clusters containing i at positions 5 or 6)/(total number of clusters of 10mers)) for central positions, j, wherein central positions are position 5 for 9mers and positions 5 and 6 for 10mers, wherein $n(i,j)$ is the number of clusters containing amino acid i at position j and $N_j=\Sigma_i\, n(i,j)$;

e) calculating a Bayes-corrected scoring matrix (BSM) from the ESM, wherein the values of the BSM (B) are calculated $B(i,j)=\log\,[\{(F(i,j)/S_i)+(e/N_j)\}/\{1+(e/N_j)\}]$ wherein $S_i$ is the frequency of occurrence of amino acid i in a protein database;

f) using the BSM to calculate a predicted binding score for a test series of candidate T-cell epitopes derived from the target protein, wherein the candidate T-cell epitopes consist of 9 or 10 amino acids, wherein the predicted binding score (S) is calculated:

(i) for each 9mer $(a_1 \ldots a_9)$, $S=\Sigma_i\, B(a_i,i)$, and (ii) for each 10mer $(a_1 \ldots a_{10})$, $S=\Sigma_{i=1,2,3,4}\, B(a_i,i)+\Sigma_i=\Sigma_{i=7,8,9,10}\, B(a_i,i)+\frac{1}{2}\{B(a_5,5)+B(a_6,6)\}$;

wherein steps d) through g) are carried out using a computer processor;

g) identifying T-cell epitopes of the target protein that are likely to bind to the MHC allele of interest, wherein the candidate T-cell epitopes of the test series having a binding score that is equal to or greater than a predetermined threshold when compared to the binding score of all other candidate T-cell epitopes in the test series are identified as T-cell epitopes likely to bind to the MHC class I allele of interest, wherein the predetermined threshold is based on a percentile at which a fraction of randomly generated peptides have a lower binding score;

h) outputting the result of at least one of steps g) and h) to at least one of a data storage system and an output device.

2. The method of claim 1 wherein the MHC class I allele is selected from the group consisting of HLA-A, HLA-B and HLA-C.

3. The method of claim 2 wherein the target protein is derived from a foreign antigen which is of viral or non-viral origin.

4. The method of claim 1 wherein the target protein is derived from a self antigen.

5. The method of claim 4 wherein the target protein is a tumor-associated antigen.

6. The method of claim 1 wherein a threshold of 65% sequence identity is used to assign the peptide sequences to the clusters.

7. The method of claim 1 wherein the method further comprises a natural processing filter which is implemented as a rule which rejects a candidate T-cell epitope peptide if it has a proline residue at position P1 or P1', or a leucine residue at position P1', wherein position P1' is the N-terminal position of the candidate epitope and position P1 is immediately preceding position P1'.

8. The method of claim 1 further comprising a self-similarity filter which is implemented as a rule which rejects a candidate T-cell epitope:
   a) if another protein in an appropriate database of reference sequences contains an amino acid sequence that is either identical to the amino acid sequence of the candidate T-cell epitope; or
   b) if another protein in an appropriate database of reference sequences contains an amino acid sequence which differs by 1 or 2 amino acids from the amino acid sequence of the candidate T-cell epitope and the mismatches are restricted to the MHC anchor residues of the candidate epitope and the reference sequence.

9. The method according to claim 1, wherein the series of candidate T-cell epitopes derived from the target protein represent all possible 9-mers and 10-mers of the target protein.

10. The method of claim 1 further comprising: i) implementing a rule which rejects a candidate T-cell epitope if another protein in an appropriate database of reference sequences contains an amino acid sequence that differs by 1 or 2 amino acids from the amino acid sequence of the candidate T-cell epitope and the differences are restricted to the MHC anchor residues of the candidate epitope and the reference sequence; wherein the rule implemented in step i) functions to eliminate candidate peptides which are not unique to the target protein.

11. The method of claim 1 further comprising: i) implementing a rule which rejects a candidate T-cell epitope: if another protein in an appropriate database of reference sequences contains an amino acid sequence that is identical to the amino acid sequence of the candidate T-cell epitope; wherein the rule implemented in step i) functions to eliminate candidate peptides which are not unique to the target protein.

12. The method of claim 1 further comprising a step of assigning the candidate T-cell epitopes a rank based on their predicted binding scores to create a ranked list.

13. The method of claim 1, wherein the predetermined threshold for selecting candidate T-cell epitopes is the $90^{th}$ percentile.

14. The method of claim 1, wherein the predetermined threshold for selecting candidate T-cell epitopes is the $95^{th}$ percentile.

* * * * *